(12) United States Patent
Kurihara et al.

(10) Patent No.: US 10,350,337 B2
(45) Date of Patent: Jul. 16, 2019

(54) VALVE AND FLUID CONTROL DEVICE

(71) Applicant: Murata Manufacturing Co., Ltd., Kyoto (JP)

(72) Inventors: Kiyoshi Kurihara, Kyoto (JP); Susumu Takeuchi, Kyoto (JP)

(73) Assignee: MURATA MANUFACTURING CO., LTD., Kyoto (JP)

( * ) Notice: Subject to any disclaimer, the term of this patent is extended or adjusted under 35 U.S.C. 154(b) by 231 days.

(21) Appl. No.: 15/345,658

(22) Filed: Nov. 8, 2016

(65) Prior Publication Data

US 2017/0072117 A1    Mar. 16, 2017

Related U.S. Application Data

(63) Continuation of application No. PCT/JP2015/063256, filed on May 8, 2015.

(30) Foreign Application Priority Data

May 13, 2014  (JP) ................................. 2014-099906
Jan. 28, 2015  (JP) ................................. 2015-014517

(51) Int. Cl.
  *A61M 1/00*  (2006.01)
  *F16K 7/17*  (2006.01)
  (Continued)

(52) U.S. Cl.
  CPC ........... *A61M 1/0035* (2014.02); *A61G 12/00* (2013.01); *A61M 1/0001* (2013.01);
  (Continued)

(58) Field of Classification Search
  CPC .............. A61M 1/0001; A61M 1/0035; A61M 1/0066; A61M 1/06; A61M 27/00;
  (Continued)

(56) References Cited

U.S. PATENT DOCUMENTS 3,633,605 A * 1/1972 Smith ..................... F15B 13/02
                                                    137/113
3,707,982 A * 1/1973 Hogel ..................... F15B 13/00
                                                    137/112

(Continued)

FOREIGN PATENT DOCUMENTS

EP      2698107 A1     2/2014
JP      63-163157 U    10/1988
                    (Continued)

OTHER PUBLICATIONS

International Search Report issued in PCT/JP2015/063256 dated Jul. 21, 2015.

(Continued)

*Primary Examiner* — Adam Marcetich
(74) *Attorney, Agent, or Firm* — Pearne & Gordon LLP

(57) ABSTRACT

A fluid control device includes a piezoelectric pump, a suction unit, and a valve. The piezoelectric pump has a suction hole for a gas and a discharge hole for the gas. The suction unit includes a container, a suction port, and a connection hole. The valve includes a first ventilation hole, a second ventilation hole, a third ventilation hole, a first valve housing, a second valve housing, and a diaphragm. The first ventilation hole of the valve is connected to the connection hole of the suction unit. The second ventilation hole of the valve is connected to the suction hole of the piezoelectric pump. The third ventilation hole of the valve is opened under atmospheric pressure. The diaphragm is clamped between the first valve housing and the second valve housing and forms a first region and a second region.

22 Claims, 14 Drawing Sheets

(51) Int. Cl.
*A61M 39/24* (2006.01)
*A61G 12/00* (2006.01)
*A61M 1/06* (2006.01)
*A61M 27/00* (2006.01)

(52) U.S. Cl.
CPC ............ *A61M 1/0066* (2013.01); *A61M 1/06* (2013.01); *A61M 27/00* (2013.01); *F16K 7/17* (2013.01)

(58) Field of Classification Search
CPC .. A61M 1/0031; A61M 1/0049; A61M 1/005; F16K 7/17
See application file for complete search history.

(56) References Cited

U.S. PATENT DOCUMENTS

| | | | | |
|---|---|---|---|---|
| 4,494,563 | A * | 1/1985 | Seiler, Jr. | F16K 17/20 137/496 |
| 4,646,781 | A * | 3/1987 | McIntyre | A61M 39/24 137/512.4 |
| 4,893,644 | A * | 1/1990 | Giacomini | F16K 15/144 137/218 |
| 6,105,608 | A * | 8/2000 | Katzman | F16K 7/17 137/202 |
| 9,033,683 | B2 | 5/2015 | Kodama et al. | |
| 9,777,974 | B2 | 10/2017 | Kamitani et al. | |
| 10,065,328 | B2 * | 9/2018 | Takeuchi | F16K 31/126 |
| 2005/0016596 | A1 * | 1/2005 | Mijers | A61M 5/36 137/512.15 |
| 2005/0161091 | A1 * | 7/2005 | Jennings | F16K 31/1266 137/510 |
| 2006/0169694 | A1 * | 8/2006 | Kemper | A47G 19/2272 220/303 |
| 2007/0006940 | A1 * | 1/2007 | Perlman | B25B 11/007 141/65 |
| 2007/0295404 | A1 * | 12/2007 | Cover | F16K 15/14 137/218 |
| 2009/0242045 | A1 * | 10/2009 | Jennings | F16K 27/0236 137/510 |
| 2009/0272922 | A1 * | 11/2009 | Bosko | F16K 7/17 251/61.1 |
| 2011/0005616 | A1 * | 1/2011 | Berglund | F16K 15/144 137/510 |
| 2012/0244454 | A1 | 9/2012 | Maeda et al. | |
| 2012/0316492 | A1 * | 12/2012 | Chappel | A61M 5/145 604/67 |
| 2013/0178752 | A1 | 7/2013 | Kodama et al. | |
| 2016/0123315 | A1 * | 5/2016 | Fukami | F04B 53/04 417/472 |

FOREIGN PATENT DOCUMENTS

| | | |
|---|---|---|
| JP | H11178915 A | 7/1999 |
| JP | 5185475 B2 | 4/2013 |
| JP | 2013074914 A | 4/2013 |
| WO | 2010137578 A1 | 12/2010 |
| WO | 2012141113 A1 | 10/2012 |
| WO | 2013/168551 A1 | 11/2013 |

OTHER PUBLICATIONS

Written Opinion issued in PCT/JP2015/063256 dated Jul. 21, 2015.
European Search Report for International Application Serial No. PCT/JP2015063256 dated Oct. 27, 2017.

* cited by examiner

VALVE AND FLUID CONTROL DEVICE

This application is a continuation of International Application No. PCT/JP2015/063256 filed on May 8, 2015 which claims priority from Japanese Patent Application No. 2015-014517 filed on Jan. 28, 2015 and Japanese Patent Application No. 2014-099906 filed on May 13, 2014. The contents of these applications are incorporated herein by reference in their entireties.

BACKGROUND OF THE DISCLOSURE

Field of the Disclosure

The present disclosure relates to a valve that switches the flow of a gas and a fluid control device that includes the valve.

Description of the Related Art

In the related art, various fluid control devices that control the flow of a gas by using a valve have been designed. For example, Patent Document 1 discloses a fluid control device that includes a pump and a valve.

The pump has an air-suction hole and an air-discharge hole.

The valve includes a diaphragm, a first valve housing, and a second valve housing and has a structure whereby the diaphragm, the first valve housing, and the second valve housing are stacked one on top of the other in this order. In addition, the valve has a ventilation hole, an exhaust port, and a cuff-connection port. The discharge hole of the pump is connected to the ventilation hole. The exhaust port is opened under atmospheric pressure. The fluid control device is connected to a cuff as a result of a manchette rubber tube of the cuff being connected to the cuff-connection port of the valve.

With the above-described configuration, the fluid control device of Patent Document 1 drives the pump and discharges air into the valve through the discharge hole of the pump. The air discharged to the valve flows into the cuff through the cuff-connection port.

In this manner, the fluid control device of Patent Document 1 fills the cuff (container) with compressed air. Then, the fluid control device of Patent Document 1 discontinues driving of the pump and causes the compressed air in the cuff (container) to be exhausted through the exhaust port.

Patent Document 1: International Publication No. 2012/141113 Pamphlet

BRIEF SUMMARY OF THE DISCLOSURE

However, the fluid control device of Patent Document 1 is not a device that causes the pressure in a container to become a negative pressure by drawing in a gas from the container. Thus, the fluid control device of Patent Document 1 is not suitable for applications, such as causing the pressure in a container to become a negative pressure by drawing in a gas from the container.

It is an object of the present disclosure to provide a valve capable of causing the pressure in a container to become a negative pressure by drawing in a gas from the container and then restoring the pressure in the container to atmospheric pressure by causing the gas to flow into the container, and to provide a fluid control device that includes the valve.

A valve according to the present disclosure has the following configuration in order to solve the above-mentioned problem.

(1) The valve according to the present disclosure includes a valve housing in which a first ventilation hole, a second ventilation hole, and a third ventilation hole are formed and a diaphragm that divides a region in the valve housing into a first region and a second region. The diaphragm is fixed to the valve housing such that the diaphragm causes the first ventilation hole and the second ventilation hole to communicate with each other and interrupts communication between the first ventilation hole and the third ventilation hole and communication between the second ventilation hole and the third ventilation hole when a pressure in the first region, which is in communication with the first ventilation hole in the valve housing, is higher than a pressure in the second region, which is in communication with the second ventilation hole in the valve housing, and such that the diaphragm causes the first ventilation hole and the third ventilation hole to communicate with each other when the pressure in the first region is lower than the pressure in the second region.

In this configuration, for example, a suction unit having a suction port is connected to the first ventilation hole. A suction hole of a pump is connected to the second ventilation hole. The third ventilation hole is opened under atmospheric pressure. In this case, when the pump is driven, the air in the second region is drawn into the pump via the second ventilation hole and the suction hole. Then, the air in the pump is discharged through a discharge hole. As a result, in the valve, the pressure in the first region becomes higher than the pressure in the second region.

In the valve, which has the above configuration, in the case where the pressure in the first region is higher than the pressure in the second region, the first ventilation hole and the second ventilation hole are caused to communicate with each other, and the communication between the first ventilation hole and the third ventilation hole and the communication between the second ventilation hole and the third ventilation hole are interrupted.

As a result, a gas in a container of the suction unit is discharged to the first region of the valve via the first ventilation hole and is drawn into the pump via the second ventilation hole and the suction hole. Consequently, the pressure (gas pressure) in the container is reduced from atmospheric pressure and becomes a negative pressure. Thus, the suction unit can suck a liquid (e.g., breast milk, blood, pleural effusion, sputum, or the like) outside the container into the container through the suction port.

Next, when driving of the pump is discontinued, the pressure in the second region is lower than atmospheric pressure, and thus, a small portion of the gas flows into the pump through the discharge hole of the pump and flows into the second region via the suction hole and the second ventilation hole. As a result, in the valve, the pressure in the first region is reduced to be lower than the pressure in the second region.

In the valve, which has the above configuration, in the case where the pressure in the first region is lower than the pressure in the second region, the first ventilation hole and the third ventilation hole are caused to communicate with each other. Then, the gas flows in through the third ventilation hole, flows out from the first ventilation hole, and flows into the container. This causes an increase in the pressure (gas pressure) in the container and restores the pressure in the container to atmospheric pressure. Accordingly, the suction port of the suction unit can be easily removed from a human breast or an animal breast.

Therefore, according to the configuration, after making the pressure in the container become a negative pressure by drawing in the gas from the container, the pressure in the container can be restored to atmospheric pressure by causing the gas to flow into the container.

(2) It is preferable that the diaphragm move into and out of contact with a portion of the valve housing due to a pressure difference between the first region and the second region and perform switching of a communication state between the first ventilation hole and the third ventilation hole.

In the above configuration, in the case where the pressure in the first region is higher than the pressure in the second region, the diaphragm comes into contact with the portion of the valve housing and interrupts the communication between the first ventilation hole and the third ventilation hole and the communication between the second ventilation hole and the third ventilation hole.

In contrast, in the case where the pressure in the first region is lower than the pressure in the second region, the diaphragm moves out of contact with the portion of the valve housing and causes the first ventilation hole and the third ventilation hole to communicate with each other.

(3) It is preferable that a first valve seat projecting toward the diaphragm in the second region be formed on the portion of the valve housing. In addition, it is preferable that a first hole be formed in the diaphragm and that the diaphragm be fixed to the valve housing such that a portion of the diaphragm around a periphery of the first hole is in contact with the first valve seat.

In the above configuration, in the case where the pressure in the first region is higher than the pressure in the second region, the diaphragm comes into contact with the first valve seat and interrupts the communication between the first ventilation hole and the third ventilation hole and the communication between the second ventilation hole and the third ventilation hole.

In contrast, in the case where the pressure in the first region is lower than the pressure in the second region, the diaphragm moves out of contact with the first valve seat and causes the first ventilation hole and the second ventilation hole to communicate with each other.

(4) It is preferable that a second valve seat projecting toward the diaphragm in the second region be formed on the portion of the valve housing. In addition, it is preferable that a third hole be formed in the second valve seat and that the diaphragm be fixed to the valve housing such that the diaphragm is in contact with the second valve seat.

In the above configuration, in the case where the pressure in the first region is higher than the pressure in the second region, the diaphragm comes into contact with the second valve seat and interrupts the communication between the first ventilation hole and the third ventilation hole and the communication between the second ventilation hole and the third ventilation hole.

In contrast, in the case where the pressure in the first region is lower than the pressure in the second region, the diaphragm moves out of contact with the second valve seat and causes the third ventilation hole and the second ventilation hole to communicate with each other.

(5) It is preferable that a third valve seat projecting toward the diaphragm in the first region be formed on the valve housing. In addition, it is preferable that a second hole be formed in the diaphragm and that the diaphragm be fixed to the valve housing such that a portion of the diaphragm around a periphery of the second hole is in contact with the third valve seat.

In the above configuration, in the case where the pressure in the first region is higher than the pressure in the second region, the diaphragm moves out of contact with the third valve seat and causes the first ventilation hole and the second ventilation hole to communicate with each other.

In contrast, in the case where the pressure in the first region is lower than the pressure in the second region, the diaphragm comes into contact with the third valve seat.

(6) A fourth ventilation hole that is in communication with the first region is formed in the valve housing.

A fluid control device according to the present disclosure has the following configuration in order to solve the above-mentioned problem.

(7) The fluid control device according to the present disclosure includes a pump that has a suction hole for a gas and a discharge hole for the gas, a suction unit that has a suction port through which a fluid is to be sucked in and a connecting portion, and the valve described in any one of the above (1) to (6). The first ventilation hole is connected to the connecting portion of the suction unit, and the second ventilation hole is connected to the suction hole of the pump.

With the above configuration, by using the valve described in any one of the above (1) to (6), advantageous effects similar to the above can be obtained by the fluid control device that includes the valve.

(8) It is preferable that the suction unit include a first container that is connected to the suction port and in which a fluid sucked in through the suction port is to be stored, a second container that is connected to the first container and that allows the gas to pass through the second container and hinders the fluid from passing through the second container, and a third container that is connected to the second container and the suction hole of the pump and that adjusts a drawing pressure at which the pump draws in the gas.

With the above configuration, the fluid control device is used as a drainage. Blood, pleural effusion, or the like that has sucked in through the suction port is stored in the first container.

According to the present disclosure, the pressure in a container can be caused to become a negative pressure by drawing in a gas from the container, and then the pressure in the container can be restored to atmospheric pressure by causing the gas to flow into the container.

BRIEF DESCRIPTION OF THE SEVERAL VIEWS OF THE DRAWINGS

FIG. 7A is a diagram illustrating a state where the capacity of a pump chamber is increased, and FIG. 7B is a diagram illustrating a state where the capacity of the pump chamber is decreased.

DETAILED DESCRIPTION OF THE DISCLOSURE

A fluid control device 100 according to a first embodiment of the present disclosure will be described below.

Figure 1:
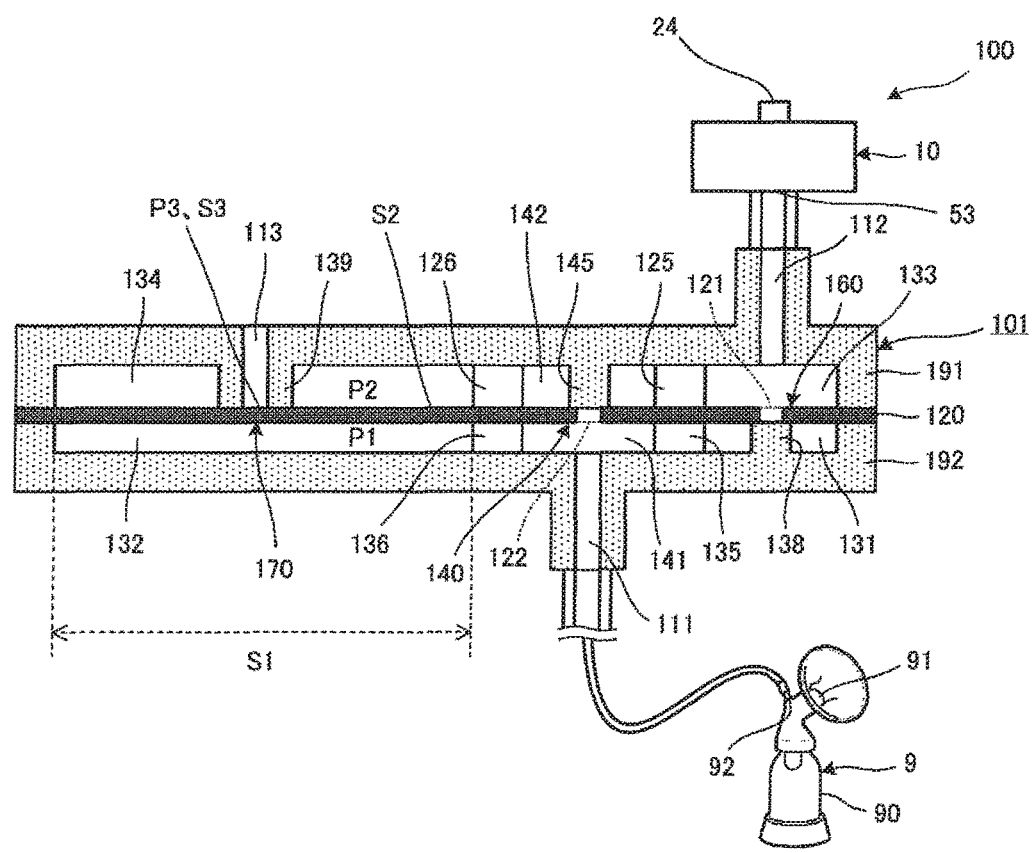
FIG. 1 is a sectional view of a principal portion of a fluid control device 100 according to a first embodiment of the present disclosure.

FIG. 1 is a sectional view of a principal portion of the fluid control device 100 according to the first embodiment of the present disclosure. The fluid control device 100 includes a piezoelectric pump 10, a suction unit 9, and a valve 101.

The piezoelectric pump 10 includes a suction hole 53 through which a gas is to be drawn in and a discharge hole 24 through which a gas is to be discharged (details of this matter will be described later).

The suction unit 9 includes a container 90, a suction port 91, and a connection hole 92. The suction unit 9 is, for example, a breast pump. The suction port 91 is placed onto, for example, a human breast or an animal breast. A liquid (e.g., breast milk or the like) is to be stored in the container 90.

The valve 101 includes a first ventilation hole 111, a second ventilation hole 112, and a third ventilation hole 113 (details of this matter will be described later). The first ventilation hole 111 of the valve 101 is connected to the connection hole 92 of the suction unit 9. The second ventilation hole 112 of the valve 101 is connected to the suction hole 53 of the piezoelectric pump 10. The third ventilation hole 113 of the valve 101 is opened under atmospheric pressure.

Note that, in FIG. 1, the connection between the first ventilation hole 111 of the valve 101 and the connection hole 92 of the suction unit 9 is illustrated in a simplified manner. Similarly, in FIG. 1, the connection between the second ventilation hole 112 of the valve 101 and the suction hole 53 of the piezoelectric pump 10 is illustrated in a simplified manner. In practice, any connecting method may be employed for these connections.

The configuration of the piezoelectric pump 10 and the configuration of the valve 101 will now be described in detail. First, the configuration of the piezoelectric pump 10 will be described in detail with reference to FIG. 2, FIG. 3, and FIG. 4.

Figure 2:
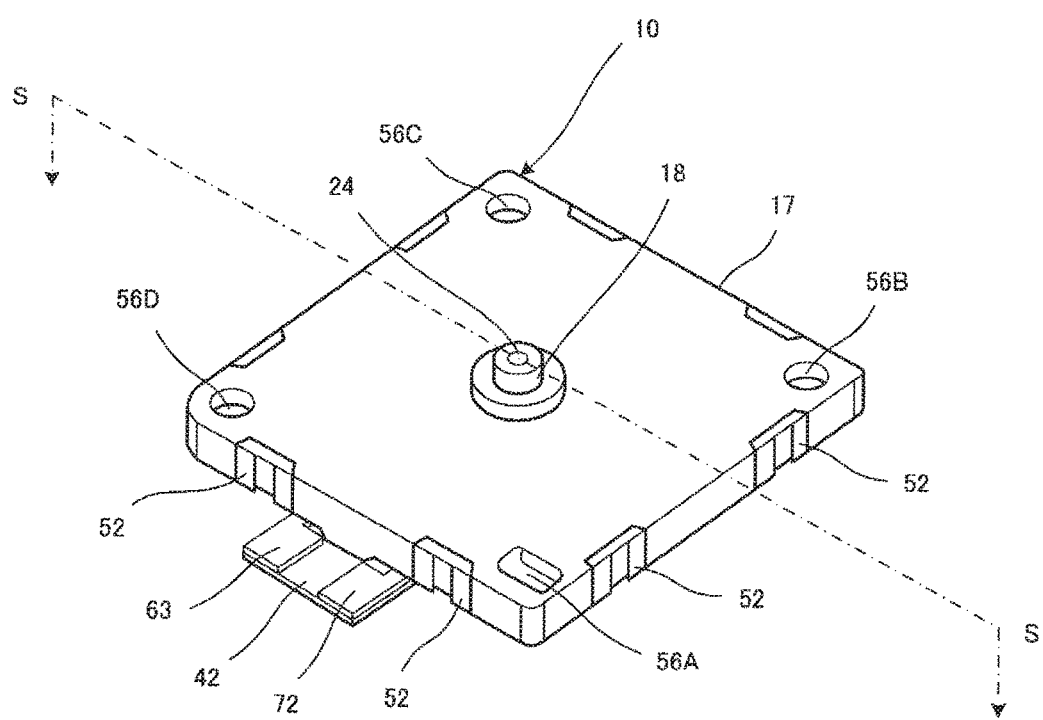
FIG. 2 is an external perspective view of a piezoelectric pump 10 illustrated in FIG. 1.
Figure 3:
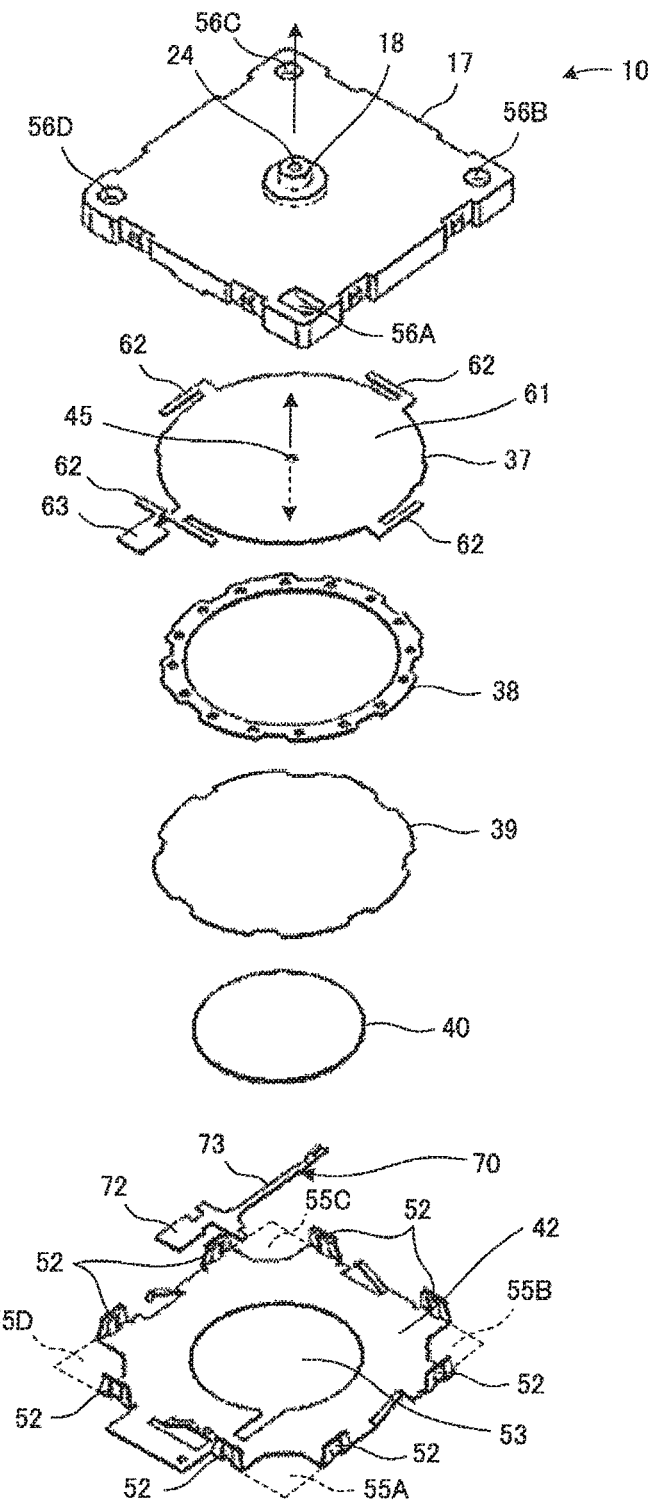
FIG. 3 is an exploded perspective view of the piezoelectric pump 10 illustrated in FIG. 2.
Figure 4:
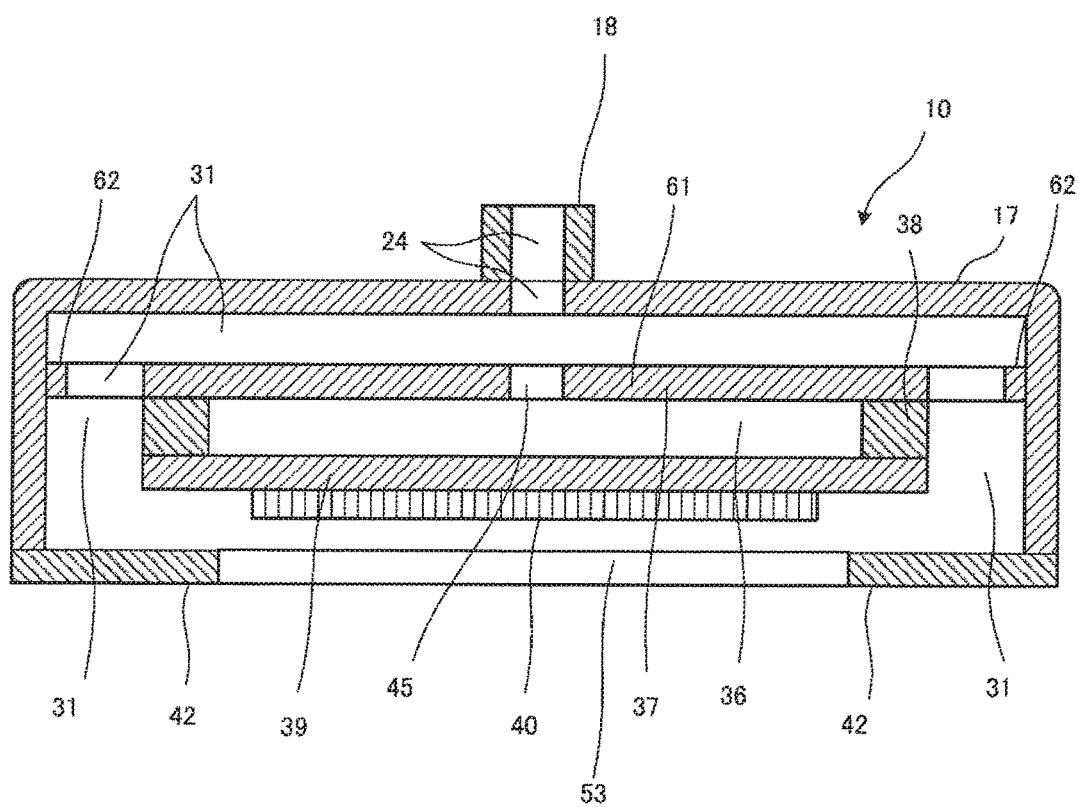
FIG. 4 is a cross-sectional view of the piezoelectric pump 10 illustrated in FIG. 2 taken along line S-S in FIG. 2.

FIG. 2 is an external perspective view of the piezoelectric pump 10 illustrated in FIG. 1. FIG. 3 is an exploded perspective view of the piezoelectric pump 10 illustrated in FIG. 2. FIG. 4 is a cross-sectional view of the piezoelectric pump 10 illustrated in FIG. 2 taken along line S-S in FIG. 2.

The piezoelectric pump 10 includes an outer housing 17, a top plate 37, a side plate 38, a vibrating plate 39, a piezoelectric element 40, and a cap 42 and has a structure whereby these members are stacked one on top of the other in this order in a top-bottom direction. The top plate 37, the side plate 38, and the vibrating plate 39 form a pump chamber 36. The piezoelectric pump 10 has dimensions (width×length×height) of 20 mm×20 mm×1.85 mm. Note that the height refers to the height of a portion of the piezoelectric pump 10 excluding a nozzle 18.

The outer housing 17 includes the nozzle 18, and the discharge hole 24 through which air is to be discharged is formed in the center of the nozzle 18. The nozzle 18 has dimensions (outer diameter× inner diameter (i.e., diameter of the discharge hole 24)× height) of 2.0 mm×0.8 mm×1.6 mm. Threaded holes 56A to 56D are formed at four corners of the outer housing 17.

The outer housing 17 is formed so as to have a U-shaped cross section while a lower portion thereof is open, and the top plate 37 of the pump chamber 36, the side plate 38 of the pump chamber 36, the vibrating plate 39, and the piezoelectric element 40 are accommodated in the outer housing 17. The outer housing 17 is formed from, for example, a resin.

The top plate 37 of the pump chamber 36 has a circular plate-like shape and is formed from, for example, a metal. The top plate 37 includes a center portion 61, hook-shaped projecting portions 62, and an external terminal 63 that is to be connected to an external circuit. Each of the hook-shaped projecting portions 62 projects from the center portion 61 in the horizontal direction and is in contact with an inner wall of the outer housing 17.

A ventilation hole 45 that causes the interior of the pump chamber 36 and the outside to communicate with each other is formed in the center portion 61 of the top plate 37. The ventilation hole 45 is formed at a position facing the discharge hole 24 of the outer housing 17. The top plate 37 is joined to a top surface of the side plate 38.

The side plate 38 of the pump chamber 36 has a ring-like shape and is formed from, for example, a metal. The side plate 38 is joined to a top surface of the vibrating plate 39. Accordingly, the thickness of the side plate 38 corresponds to the height of the pump chamber 36.

The vibrating plate 39 has a circular plate-like shape and is formed from, for example, a metal. The vibrating plate 39 forms a bottom surface of the pump chamber 36.

The piezoelectric element 40 has a circular plate-like shape and is formed from, for example, a PZT-based ceramic. The piezoelectric element 40 is joined to a main surface of the vibrating plate 39, the main surface being located on the side opposite to the side on which the pump chamber 36 is present, and bends in response to an alternating-current (AC) voltage being applied to the piezoelectric element 40. The piezoelectric element 40 and the vibrating plate 39 form an actuator.

A unified body formed of the top plate 37, the side plate 38, the vibrating plate 39, and the piezoelectric element 40 is elastically supported by the four projecting portions 62 of the top plate 37 with respect to the outer housing 17.

An electrode-conduction plate 70 includes an inner terminal 73 that is to be connected to the piezoelectric element 40 and an outer terminal 72 that is to be connected to the external circuit. An end of the inner terminal 73 is soldered to a flat-plate surface of the piezoelectric element 40. By setting the position at which the end of the inner terminal 73 is soldered to a position corresponding to a node of bending vibration of the piezoelectric element 40, vibration of the inner terminal 73 can be further suppressed.

A suction hole 53 having a circular plate-like shape is formed in the cap 42. The diameter of the suction hole 53 is larger than the diameter of the piezoelectric element 40. In the cap 42, cutout portions 55A to 55D are formed at positions corresponding to the threaded holes 56A to 56D of the outer housing 17.

The cap 42 includes projecting portions 52 that are formed at the outer peripheral edge of the cap 42 and that project toward the top plate 37. The cap 42 clamps the outer housing 17 by the projecting portions 52 and accommodates, together with the outer housing 17, the top plate 37 of the pump chamber 36, the side plate 38 of the pump chamber 36, the vibrating plate 39, and the piezoelectric element 40. The cap 42 is formed from, for example, a resin.

As illustrated in FIG. 4, a ventilation path 31 is formed between the unified body, which is formed of the top plate 37, the side plate 38, the vibrating plate 39, and the piezoelectric element 40, and the outer housing 17 and the cap 42.

The configuration of the valve 101 will now be described in detail with reference to FIG. 1, FIG. 5, and FIG. 6.

Figure 5:
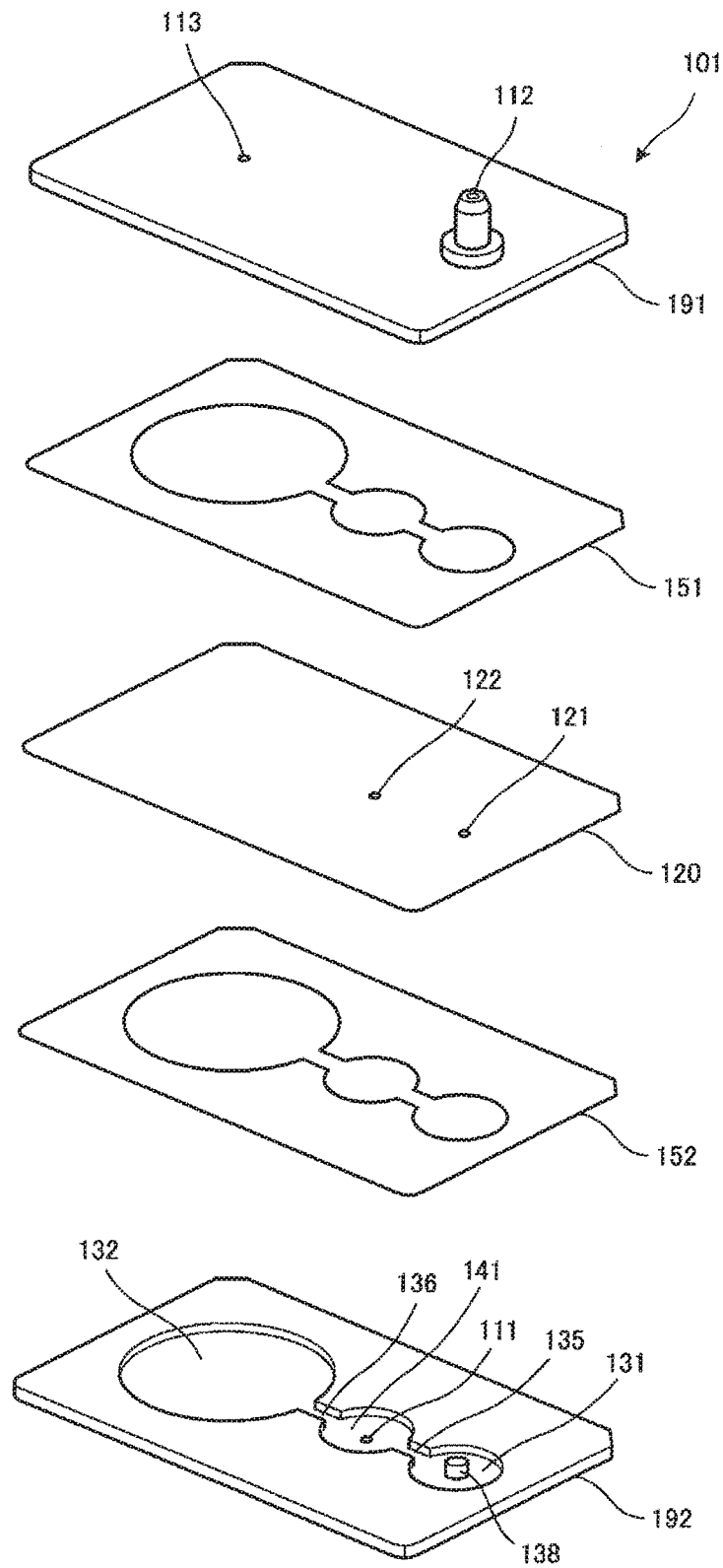
FIG. 5 is an exploded perspective view of a valve 101 illustrated in FIG. 1.
Figure 6:
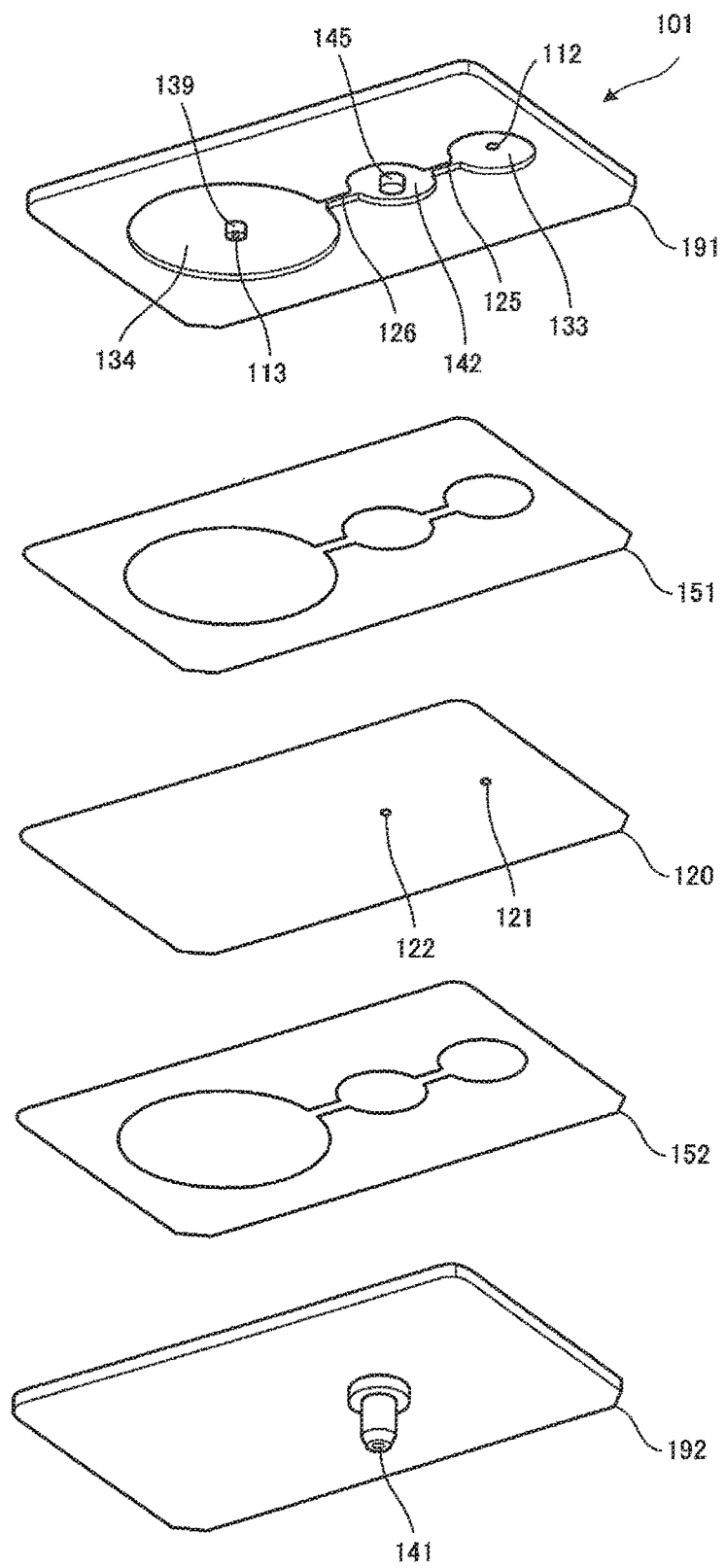
FIG. 6 is an exploded perspective view of the valve 101 illustrated in FIG. 1.

FIG. 5 and FIG. 6 are exploded perspective views of the valve 101 illustrated in FIG. 1. FIG. 5 is an exploded perspective view of the valve 101 when viewed from the top surface side of the valve 101, and FIG. 6 is an exploded perspective view of the valve 101 when viewed from the bottom surface side of the valve 101.

As illustrated in FIG. 1, FIG. 5, and FIG. 6, the valve 101 includes a second valve housing 192, a second seal member 152, a diaphragm 120, a first seal member 151, and a first valve housing 191 and has a structure whereby these members are stacked one on top of the other in this order.

As illustrated in FIG. 1, FIG. 5, and FIG. 6, the first valve housing 191 includes the second ventilation hole 112, the third ventilation hole 113, a valve seat 139, a valve seat 145, a communication path 125, and a communication path 126. The second ventilation hole 112 is in communication with the suction hole 53 of the piezoelectric pump 10. The third ventilation hole 113 is in communication with the outside of the fluid control device 100. The valve seat 139 projects from the periphery of the third ventilation hole 113 toward the diaphragm 120. The valve seat 145 has a columnar shape and projects toward the diaphragm 120. The communication path 125 causes a first upper valve chamber 142 and a second upper valve chamber 133 to communicate with each other. The communication path 126 causes the first upper valve chamber 142 and a third upper valve chamber 134 to communicate with each other. The first valve housing 191 is formed from, for example, a resin. The valve seat 139 has a cylindrical shape, and the third ventilation hole 113 is formed in a center portion of the valve seat 139.

As illustrated in FIG. 1, FIG. 5, and FIG. 6, the second valve housing 192 includes the first ventilation hole 111, a valve seat 138, a communication path 135, and a communication path 136. The first ventilation hole 111 is in communication with the connection hole 92 of the suction unit 9. The valve seat 138 has a columnar shape and projects toward the diaphragm 120. The communication path 135 causes a first lower valve chamber 141 and a second lower valve chamber 131 to communicate with each other. The communication path 136 causes the first lower valve chamber 141 and a third lower valve chamber 132 to communicate with each other. The second valve housing 192 is formed from, for example, a resin.

As illustrated in FIG. 1, FIG. 5, and FIG. 6, in the diaphragm 120, a circular hole 121 is formed at the center of a region facing the valve seat 138. The diameter of the hole 121 is set to be smaller than the diameter of a surface of the valve seat 138, which is in contact with the diaphragm 120.

In addition, in the diaphragm 120, a circular hole 122 is formed at the center of a region facing the valve seat 145 as illustrated in FIG. 1, FIG. 5, and FIG. 6. The diameter of the hole 122 is set to be smaller than the diameter of a surface of the valve seat 145, which is in contact with the diaphragm 120.

The diaphragm 120 is formed of a thin film having a rectangular shape. The material of the diaphragm 120 is, for example, a rubber such as ethylene propylene diene monomer (EPDM) rubber or a silicone rubber.

The diaphragm 120 is clamped between the first valve housing 191 and the second valve housing 192 with the first seal member 151 interposed between the first valve housing 191 and the diaphragm 120 and with the second seal member 152 interposed between the second valve housing 192 and the diaphragm 120.

Each of the first seal member 151 and the second seal member 152 is formed of a thin film having a rectangular shape. The material of each of the first seal member 151 and the second seal member 152 is, for example, a double-sided adhesive tape or an adhesive. In the first seal member 151, an opening is formed in a region facing the first upper valve chamber 142, the communication path 125, the second upper valve chamber 133, the communication path 126, and the third upper valve chamber 134. In the second seal member 152, an opening is formed in a region facing the first lower valve chamber 141, the communication path 135, the second lower valve chamber 131, the communication path 136, and the third lower valve chamber 132.

As illustrated in FIG. 1, the diaphragm 120 is fixed to the first valve housing 191 and the second valve housing 192 such that a portion of the diaphragm 120 around the periphery of the hole 121 is in contact with the valve seat 138, and that a portion of the diaphragm 120 around the periphery of the hole 122 is in contact with the valve seat 145. In this case, the valve seat 138 pressurizes the portion of the diaphragm 120 around the periphery of the hole 121. The valve seat 145 pressurizes the portion of the diaphragm 120 around the periphery of the hole 122.

The diaphragm 120 divides a region enclosed by the first valve housing 191 and the second valve housing 192 as a result of being fixed to the first valve housing 191 and the second valve housing 192.

Accordingly, in the region enclosed by the first valve housing 191 and the second valve housing 192, the diaphragm 120 forms the first lower valve chamber 141 having a columnar shape, the second lower valve chamber 131 having a ring-like shape, the third lower valve chamber 132 having a columnar shape, the first upper valve chamber 142 having a ring-like shape, the second upper valve chamber 133 having a columnar shape, and the third upper valve chamber 134 having a ring-like shape.

Here, the first lower valve chamber 141 is in communication with the first ventilation hole 111. The second lower valve chamber 131 is in communication with the first lower valve chamber 141 via the communication path 135. The third lower valve chamber 132 is in communication with the first lower valve chamber 141 via the communication path 136. The second upper valve chamber 133 is in communication with the first upper valve chamber 142 via the communication path 125 and is in communication with the second ventilation hole 112. The third upper valve chamber 134 is in communication with the first upper valve chamber 142 via the communication path 126.

Note that the first lower valve chamber 141, the communication path 135, the second lower valve chamber 131, the communication path 136, and the third lower valve chamber 132 correspond to a first region according to the present disclosure. The first upper valve chamber 142, the communication path 125, the second upper valve chamber 133, the communication path 126, and the third upper valve chamber 134 correspond to a second region according to the present disclosure. The valve seat 145 corresponds to a first valve seat according to the present disclosure. The valve seat 139 corresponds to a second valve seat according to the present disclosure. The valve seat 138 corresponds to a third valve seat according to the present disclosure. The hole 122 corresponds to a first hole according to the present disclosure. The hole 121 corresponds to a second hole according to the present disclosure.

The diaphragm 120 forms, together with the first valve housing 191 and the second valve housing 192, a check valve 140. The check valve 140 is formed of the first lower valve chamber 141, the first upper valve chamber 142, the valve seat 145, a portion of the diaphragm 120 facing the first lower valve chamber 141, and a portion of the diaphragm 120 facing the first upper valve chamber 142.

In addition, the diaphragm 120 forms, together with the first valve housing 191 and the second valve housing 192, a check valve 160. The check valve 160 is formed of the second lower valve chamber 131, the second upper valve chamber 133, the valve seat 138, a portion of the diaphragm 120 facing the second lower valve chamber 131, and a portion of the diaphragm 120 facing the second upper valve chamber 133.

Furthermore, the diaphragm 120 forms, together with the first valve housing 191 and the second valve housing 192, an exhaust valve 170. The exhaust valve 170 is formed of the third lower valve chamber 132, the third upper valve chamber 134, the valve seat 139, a portion of the diaphragm 120 facing the third lower valve chamber 132, and a portion of the diaphragm 120 facing the third upper valve chamber 134.

In the check valve 140, the diaphragm 120 moves into and out of contact with the valve seat 145 due to a pressure difference between the first lower valve chamber 141 and the first upper valve chamber 142. As a result, the check valve 140 enables the flow of the air from the first upper valve chamber 142 toward the first lower valve chamber 141 and interrupts the flow of the air from the first lower valve chamber 141 toward the first upper valve chamber 142.

In the check valve 160, the diaphragm 120 moves into and out of contact with the valve seat 138 due to a pressure difference between the second lower valve chamber 131 and the second upper valve chamber 133. As a result, the check valve 160 enables the flow of the air from the second lower valve chamber 131 toward the second upper valve chamber 133 and interrupts the flow of the air from the second upper valve chamber 133 toward the second lower valve chamber 131.

When the area of the portion of the diaphragm 120 facing the third lower valve chamber 132 is denoted by S1, the pressure in the third lower valve chamber 132 is denoted by P1, the area of the portion of the diaphragm 120 facing the third upper valve chamber 134 is denoted by S2, the pressure in the third upper valve chamber 134 is denoted by P2, the area of a portion of the diaphragm 120 facing the third ventilation hole 113 is denoted by S3, and the pressure in the third ventilation hole 113 (atmospheric pressure according to the present embodiment) is denoted by P3, in the case where a relationship of $S1 \times (P1-P2) > S3 \times (P3-P1)$ is satisfied, as illustrated in FIG. 1, the diaphragm 120 moves into contact with the valve seat 139 in the exhaust valve 170. Conversely, in the case where a relationship of $S1 \times (P1-P2) \leq S3 \times (P3-P1)$ is satisfied, the diaphragm 120 moves out of contact with the valve seat 139. In other words, the diaphragm 120 moves into and out of contact with the valve seat 139 synchronously with switching of the piezoelectric pump 10 on and off. As a result, the pressure in the container 90 of the suction unit 9 automatically changes synchronously with switching of the piezoelectric pump 10 on and off.

As illustrated in FIG. 5 and FIG. 6, in the valve 101, the external shape of each of the valve chambers 131, 132, 133, 134, 141, and 142 is a circular shape, and thus, tension is applied uniformly to the diaphragm 120 (particularly the portions of the diaphragm 120 around the periphery of the holes 121 and 122).

Therefore, the probability of the diaphragm 120 being in contact with the valve seat 138 in a state where the hole 121 of the diaphragm 120 is inclined with respect to the valve seat 138 and the probability of the hole 121 of the diaphragm 120 being displaced with respect to the valve seat 138 in the horizontal direction are reduced.

Similarly, the probability of the diaphragm 120 being in contact with the valve seat 145 in a state where the hole 122 of the diaphragm 120 is inclined with respect to the valve seat 145 and the probability of the hole 122 of the diaphragm 120 being displaced with respect to the valve seat 145 in the horizontal direction are reduced. Therefore, according to the valve 101, opening and closing of each of the valves can be performed with higher certainty.

Operation of the piezoelectric pump 10 during the period when the piezoelectric pump 10 is driven will now be described.

Figure 7A:
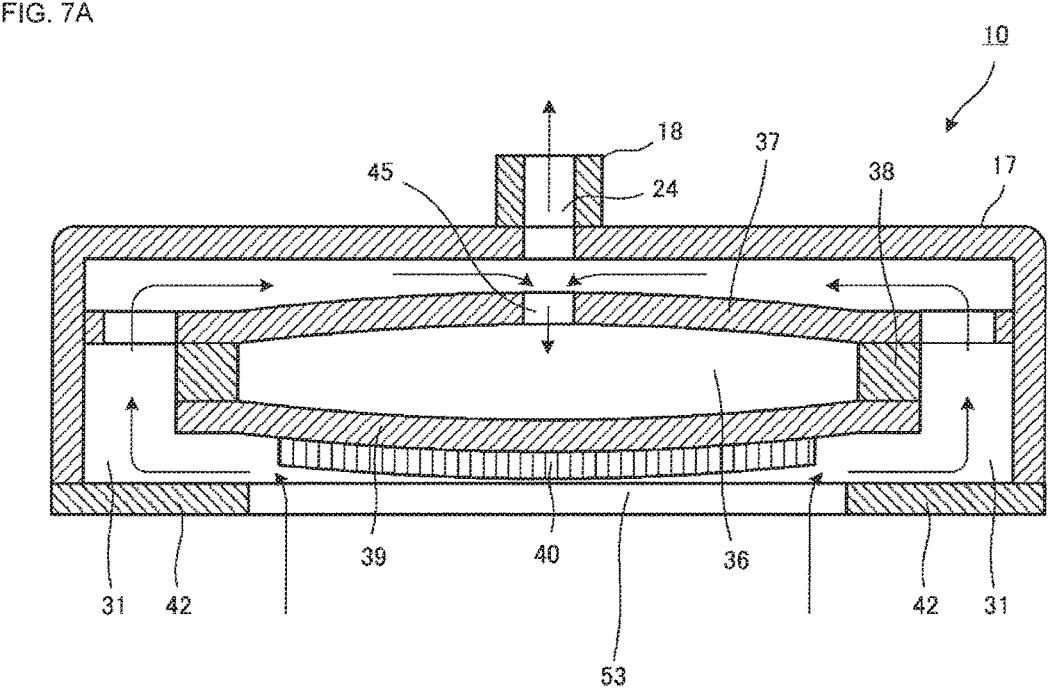
FIGS. 7A and 7B are cross-sectional views of the piezoelectric pump 10 illustrated in FIG. 2 taken along line S-S of FIG. 2 when the piezoelectric pump 10 is caused to operate in a first mode.
Figure 7B:
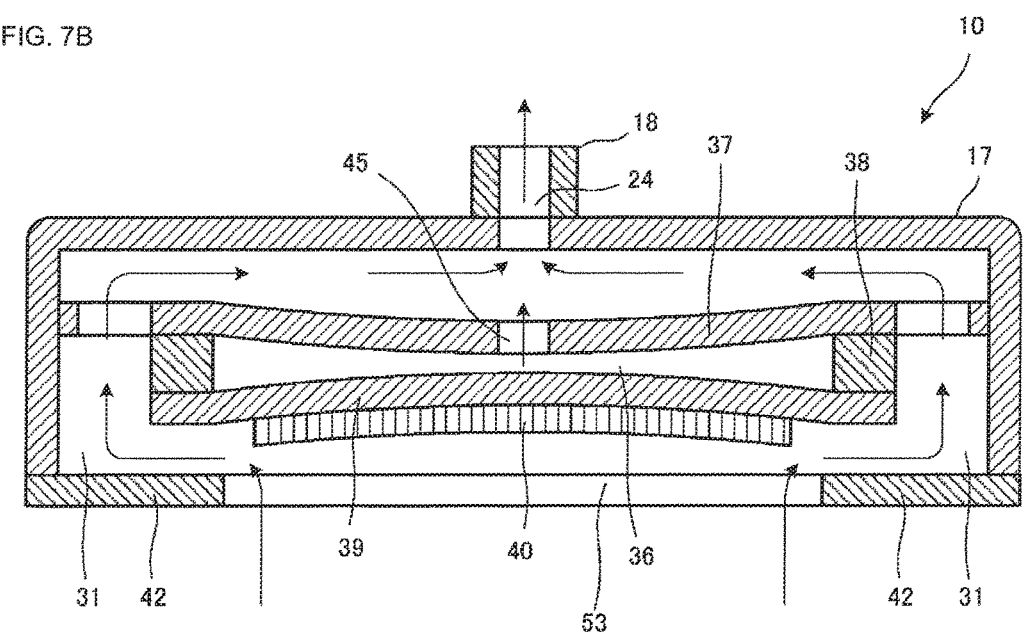

FIGS. 7A and 7B are cross-sectional views of the piezoelectric pump 10 illustrated in FIG. 1 taken along line S-S when the piezoelectric pump 10 is caused to operate at a first mode frequency (fundamental wave). Here, arrows in FIGS. 7A and 7B indicate the flow of air.

In the state illustrated in FIG. 4, when an AC drive voltage at the first mode frequency (fundamental wave) is applied to the piezoelectric element 40 through the external terminals 63 and 72, the vibrating plate 39 performs concentric circular bending vibration. At the same time, pressure fluctuations in the pump chamber 36 along with the bending vibration of the vibrating plate 39 causes the top plate 37 to perform concentric circular bending vibration along with the bending vibration of the vibrating plate 39 (with a vibration phase delay of 180 degrees according to the present embodiment).

As a result, as illustrated in FIGS. 7A and 7B, the vibrating plate 39 and the top plate 37 are bent and deformed, and the volume of the pump chamber 36 periodically changes.

As illustrated in FIG. 7A, when an AC voltage is applied to the piezoelectric element 40 so as to cause the vibrating plate 39 to bend toward the piezoelectric element 40, the capacity of the pump chamber 36 is increased. Along with this, the air outside the piezoelectric pump 10 is drawn into the pump chamber 36 via the suction hole 53, the ventilation path 31, and the ventilation hole 45. While the air is not flowing out from the pump chamber 36, an inertial force of the flow of the air from the discharge hole 24 toward the outside of the piezoelectric pump 10 is generated.

As illustrated in FIG. 7B, when an AC voltage is applied to the piezoelectric element 40 so as to cause the vibrating plate 39 to bend toward the pump chamber 36, the capacity of the pump chamber 36 is decreased. Along with this, the air in the pump chamber 36 is discharged from the discharge hole 24 via the ventilation hole 45 and the ventilation path 31.

In this case, the air discharged from the pump chamber 36 is discharged through the discharge hole 24 while the air outside the piezoelectric pump 10 is drawn in via the suction hole 53 and the ventilation path 31. Thus, in the piezoelectric pump 10, the flow rate of the air that is discharged through the discharge hole 24 is increased by the flow rate of the air that is drawn in.

The flow of the air in the fluid control device 100 will now be described.

Figure 8:
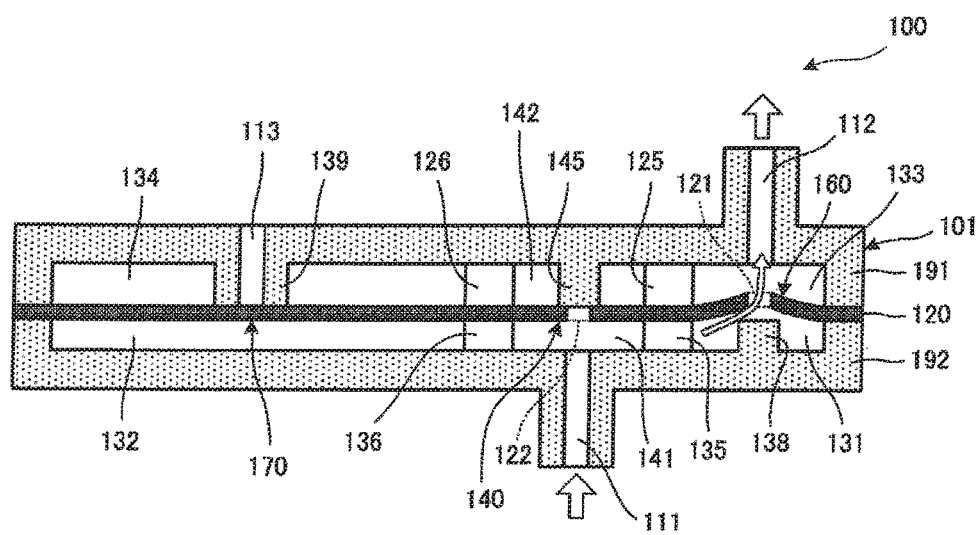
FIG. 8 is a diagram illustrating the flow of the air in the fluid control device 100 during the period when the piezoelectric pump 10 is driven.

FIG. 8 is a diagram illustrating the flow of the air in the fluid control device 100 during the period when the piezoelectric pump 10 is driven. Arrows in FIG. 8 indicate the flow of the air. In FIG. 8, the piezoelectric pump 10 and the suction unit 9 are not illustrated.

Note that, as described above, the first lower valve chamber 141, the communication path 135, the second lower valve chamber 131, the communication path 136, and the third lower valve chamber 132 correspond to the first region according to the present disclosure. The first upper valve chamber 142, the communication path 125, the second upper valve chamber 133, the communication path 126, and the third upper valve chamber 134 correspond to the second region according to the present disclosure. The valve seat 145 corresponds to the first valve seat according to the present disclosure. The valve seat 139 corresponds to the second valve seat according to the present disclosure. The valve seat 138 corresponds to the third valve seat according to the present disclosure. The hole 122 corresponds to the first hole according to the present disclosure. The hole 121 corresponds to the second hole according to the present disclosure.

First, a user places the suction port 91 of the suction unit 9 onto, for example, a human breast or an animal breast. The pressure in the container 90 before the piezoelectric pump 10 is driven is at atmospheric pressure. The fluid control device 100 switches the piezoelectric pump 10 on when suction of a liquid using the suction unit 9 is started.

Once the piezoelectric pump 10 has been driven, the air in the second upper valve chamber 133 is drawn into the piezoelectric pump 10 via the second ventilation hole 112 and the suction hole 53. Then, the air in the piezoelectric pump 10 is discharged through the discharge hole 24.

As a result, in the check valve 160, the pressure in the second lower valve chamber 131 is higher than the pressure in the second upper valve chamber 133. Thus, in the check valve 160, the portion of the diaphragm 120 around the periphery of the hole 121 moves out of contact with the valve seat 138, and the first ventilation hole 111 and the second ventilation hole 112 are caused to communicate with each other via the hole 121.

In the check valve 140, the pressure in the first lower valve chamber 141 is higher than the pressure in the first upper valve chamber 142. Thus, the portion of the diaphragm 120 around the periphery of the hole 122 is maintained in contact with the valve seat 145 and interrupts the communication between the first lower valve chamber 141 and the first upper valve chamber 142.

In contrast, in the exhaust valve 170, the pressure in the third lower valve chamber 132 is higher than the pressure in the third upper valve chamber 134. Thus, the diaphragm 120 seals the third ventilation hole 113 and interrupts the communication between the second ventilation hole 112 and the third ventilation hole 113.

In other words, in the valve 101, in the case where the pressure in the first region is higher than the pressure in the second region, the first ventilation hole 111 and the second ventilation hole 112 are caused to communicate with each other, and the communication between the first ventilation hole 111 and the third ventilation hole 113 and the communication between the second ventilation hole 112 and the third ventilation hole 113 are interrupted.

As a result, the air in the container 90 of the suction unit 9 is discharged from the connection hole 92 toward the first lower valve chamber 141 of the valve 101 via the first ventilation hole 111. Consequently, the pressure (air pressure) in the container 90 is reduced to be lower than atmospheric pressure and becomes a negative pressure.

Therefore, the suction unit 9 can suck a liquid (e.g., breast milk or the like) outside the container 90 into the container 90 through the suction port 91. The suction unit 9 stores the liquid in the container 90 and discharges the air in the container 90 through the connection hole 92.

Note that the air discharged to the first lower valve chamber 141 flows into the second upper valve chamber 133 via the communication path 135, the second lower valve chamber 131, and the hole 121. Then, the air in the second upper valve chamber 133 is drawn into the piezoelectric pump 10 via the second ventilation hole 112 and the suction hole 53 and is discharged through the discharge hole 24.

Figure 9:
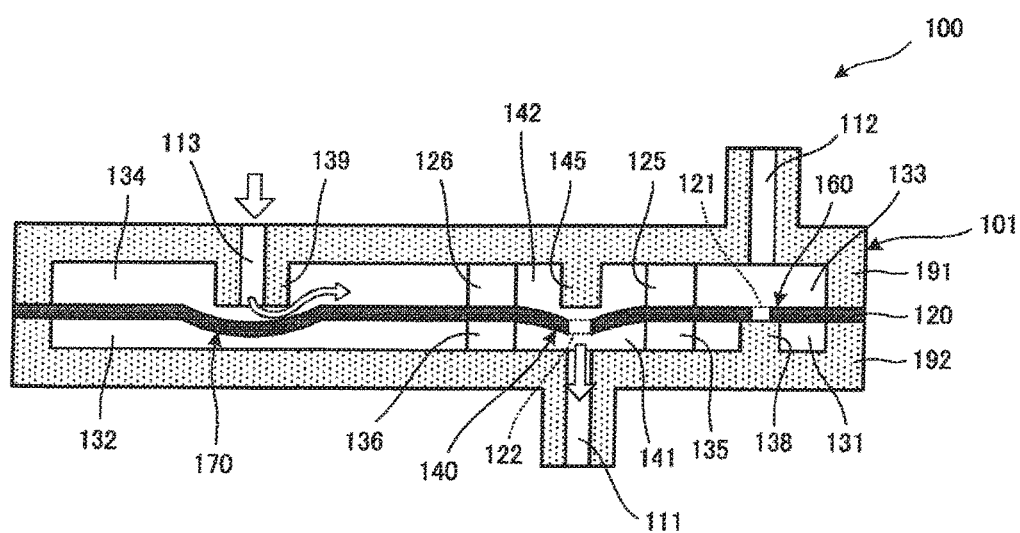
FIG. 9 is a diagram illustrating the flow of the air in the fluid control device 100 immediately after driving of the piezoelectric pump 10 has been discontinued.

FIG. 9 is a diagram illustrating the flow of the air in the fluid control device 100 immediately after driving of the piezoelectric pump 10 has been discontinued. Arrows in FIG. 9 indicate the flow of the air. In FIG. 9, the piezoelectric pump 10 and the suction unit 9 are not illustrated.

When suction of a liquid using the suction unit 9 is terminated, the fluid control device 100 switches the piezoelectric pump 10 off and discontinues driving of the piezoelectric pump 10. In this case, since the pressure in the second region is lower than atmospheric pressure, a small portion of the air flows into the piezoelectric pump 10 through the discharge hole 24 of the piezoelectric pump 10 and flows into the second region via the suction hole 53 and the second ventilation hole 112.

As a result, in the check valve 160, the pressure in the second lower valve chamber 131 is reduced to be lower than the pressure of the second upper valve chamber 133. Consequently, the diaphragm 120 closes the hole 121 by coming into contact with the valve seat 138.

In the check valve 140, the pressure in the first lower valve chamber 141 is reduced to be lower than the pressure in the first upper valve chamber 142. Consequently, the portion of the diaphragm 120 around the periphery of the hole 122 moves out of contact with the valve seat 145 and causes the first ventilation hole 111 and the second region to communicate with each other.

In contrast, in the exhaust valve 170, the pressure of the third lower valve chamber 132 is reduced to be lower than the pressure in the third upper valve chamber 134. Consequently, the diaphragm 120 opens the third ventilation hole 113 by moving out of contact with the valve seat 139.

In other words, in the valve 101, in the case where the pressure in the first region is lower than the pressure in the second region, the first ventilation hole 111 and the third ventilation hole 113 communicate with each other. As a result, the air rapidly flows through the third ventilation hole 113 into the container 90 via the third upper valve chamber 134, the communication path 126, the first upper valve chamber 142, the hole 122, the first lower valve chamber 141, and the first ventilation hole 111 (see FIG. 9).

This causes an increase in the pressure (air pressure) in the container 90 and restores the pressure in the container 90 to atmospheric pressure. Accordingly, the suction port 91 of the suction unit 9 can be easily removed from a human breast or an animal breast.

Therefore, according to the valve 101 of the present embodiment, after making the pressure in the container 90 become a negative pressure by drawing in the air from the container 90, the pressure in the container 90 can be rapidly restored to atmospheric pressure by causing the air to flow into the container 90. In addition, advantageous effects similar to the above can be obtained by the fluid control device 100 that includes the valve 101 according to the present embodiment.

A fluid control device 200 according to a second embodiment of the present disclosure will be described below.

Figure 10:
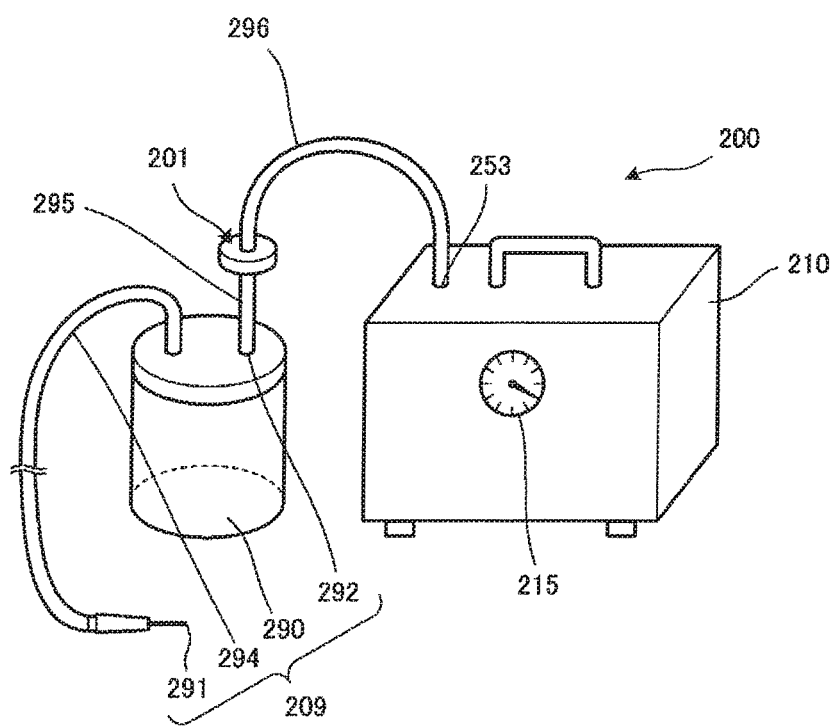
FIG. 10 is a diagram illustrating the appearance of a fluid control device 200 according to a second embodiment of the present disclosure.
Figure 11:
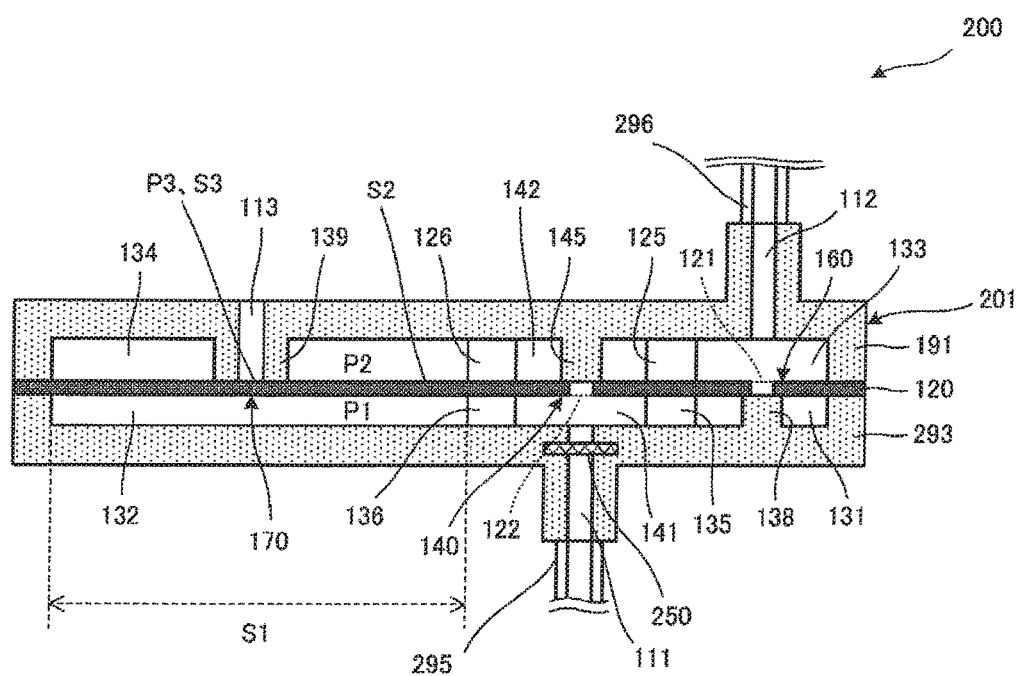
FIG. 11 is a cross-sectional view of a valve 201 illustrated in FIG. 10.

FIG. 10 is a diagram illustrating the appearance of the fluid control device 200 according to the second embodiment of the present disclosure. FIG. 11 is a cross-sectional view of a valve 201 illustrated in FIG. 10. The fluid control device 200 is a device that sucks in a liquid (e.g., sputum or the like). The fluid control device 200 includes a pump 210, a suction unit 209, and the valve 201.

The pump 210 includes a suction hole 253 that is used for drawing in air, a discharge hole (not illustrated) that is used for discharging the air, and a pressure gauge 215 that shows an air-drawing pressure.

The suction unit 209 includes a container 290, a connection hole 292, and a tube 294. A suction port 291, which is an end portion of the tube 294, is inserted into, for example, a human oral cavity or an animal oral cavity. A liquid (e.g., sputum or the like) is to be stored in the container 290.

Note that the connection hole 292 corresponds to an example of a connecting portion according to the present disclosure.

The difference between the valve 201 and the valve 101 is that the valve 201 includes a filter 250 in a second housing 293. The difference between the second valve housing 293 of the valve 201 and the second housing 192 of the valve 101 is that a space in which the filter 250 is disposed is formed in the second housing 293. The rest of the configuration of the valve 201 is the same as that of the valve 101.

The filter 250 allows a gas to pass therethrough and hinders a liquid from passing therethrough. In order to prevent infection and contamination, the filter 250 sucks in, for example, a bacterium. The filter 250 is bonded to the inner wall of the second housing 293 with an adhesive or the like.

In the above-described configuration, the suction port 291 is connected to the container 290 via the tube 294. The first ventilation hole 111 of the valve 201 is connected to the connection hole 292 of the suction unit 209 via a tube 295. The second ventilation hole 112 of the valve 201 is connected to the suction hole 253 of the pump 210 via a tube 296. The third ventilation hole 113 of the valve 201 is released under atmospheric pressure.

Note that, as described above, the first lower valve chamber 141, the communication path 135, the second lower valve chamber 131, the communication path 136, and the third lower valve chamber 132 correspond to the first region according to the present disclosure. The first upper valve chamber 142, the communication path 125, the second upper valve chamber 133, the communication path 126, and the third upper valve chamber 134 correspond to the second region according to the present disclosure. The valve seat 145 corresponds to the first valve seat according to the present disclosure. The valve seat 139 corresponds to the second valve seat according to the present disclosure. The valve seat 138 corresponds to the third valve seat according to the present disclosure. The hole 122 corresponds to the first hole according to the present disclosure. The hole 121 corresponds to the second hole according to the present disclosure.

The flow of the air in the fluid control device 200 during the period when the pump 210 is driven is substantially the same as the flow of the air in the fluid control device 100 illustrated in FIG. 8. In the fluid control device 200, the air flows by passing through the filter 250.

The flow of the air in the fluid control device 200 when driving of the pump 210 is discontinued, when the pressure in the container 290 reaches a maximum drawing pressure of the pump 210, or when a flow path is blocked is also substantially the same as the flow of the air in the fluid control device 100 illustrated in FIG. 9. In the fluid control device 200, the air flows by passing through the filter 250.

For example, the suction port 291 is blocked if human body tissue is sucked in through the suction port 291 in a state where there is no target to be sucked in. As a result of the suction port 291 being blocked, the pressure in the first region becomes equal to or lower than the pressure in the second region. When the pressure in the first region has become equal to or lower than the pressure in the second region, as illustrated in FIG. 9, the diaphragm 120 automatically opens the third ventilation hole 113 and the hole 122, and the suction port 291 is released under atmospheric pressure.

Accordingly, the valve 201 can obtain advantageous effects similar to those of the valve 101. In other words, the valve 201 can cause the pressure in the container 290 to become a negative pressure by drawing in the air from the container 290 and then can rapidly restore the pressure in the container 290 to atmospheric pressure by causing the air to flow into the container 290. In addition, advantageous effects similar to the above can be obtained by the fluid control device 200 that includes the valve 201.

Here, in the case where a liquid adheres to the filter 250 during the period when the pump 210 is driven, the filter 250 becomes clogged, and the flow path resistance (air-flow resistance) of the filter 250 increases. In other words, the fluid control device 200 cannot properly draw in the air.

Although a common suction device of the related art also includes a filter, the suction device cannot detect a situation in which the filter has become clogged. A filter in a suction device of the related art is replaced by a nurse or the like who checks the appearance of the filter or manages the length of time the filter is used. In other words, in a suction device of the related art, it is difficult to perform quantitative management of a filter.

In contrast, in the valve 201 of the fluid control device 200, as a result of the flow path resistance of the filter 250 being increased, there will be no pressure difference between the first region and the second region, and the diaphragm 120 opens the third ventilation hole 113 and the hole 122. As a result of the third ventilation hole 113 and the hole 122 being opened under atmospheric pressure, noise is generated when the air passes through the third ventilation hole 113 and the hole 122.

Thus, in the valve 201 and the fluid control device 200, noise that is generated when the third ventilation hole 113 and the hole 122 are opened under atmospheric pressure enables a nurse or the like to easily detect a situation in which the filter 250 has become clogged.

A fluid control device 300 according to a third embodiment of the present disclosure will be described below.

Figure 12:
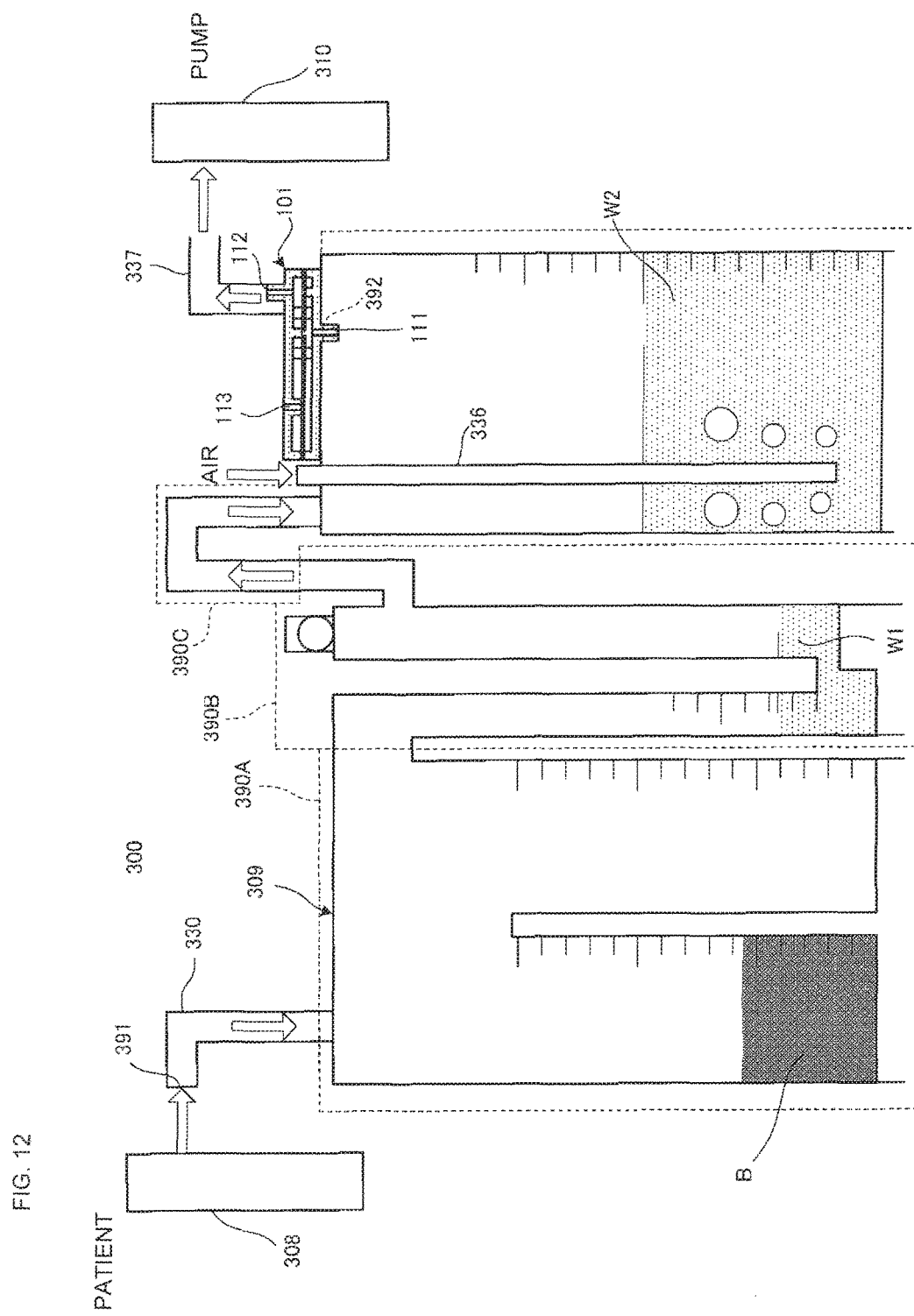
FIG. 12 is a diagram illustrating the appearance of a fluid control device 300 according to a third embodiment of the present disclosure.

FIG. 12 is a sectional view of the fluid control device 300 according to the third embodiment of the present disclosure. Arrows in FIG. 12 indicate the flow of a fluid. The fluid control device 300 is a drainage that sucks in a liquid (e.g., pleural effusion, blood, or the like). The fluid control device 300 includes a pump 310, a suction unit 309, and the valve 101.

The pump 310 may be any pump and has a suction hole (not illustrated) used for drawing in air and a discharge hole (not illustrated) used for discharging the air.

The suction unit 309 is a so-called chest drain bag. The suction unit 309 includes a first container 390A, a second container 390B, a third container 390C, a tube 330, a connection hole 392, and the tube 337. A suction port 391, which is an end portion of the tube 337, is inserted into the chest cavity of a patient 308. The patient 308 is, for example, a human or an animal.

Note that the connection hole 392 corresponds to an example of the connecting portion according to the present disclosure.

The first container 390A is a so-called drainage bottle. The first container 390A is connected to the suction port 391. A liquid B (e.g., pleural effusion, blood, or the like) of the patient 308 that is sucked in through the suction port 391 is to be stored in the first container 390A.

The second container 390B is a so-called water-sealed bottle. The second container 390B is connected to the first container 390A. Water W1 is stored in the second container 390B. By using the water W1, the second container 390B allows the air to pass therethrough and hinders the liquid B from passing therethrough.

The third container 390C is a so-called drawing-pressure control bottle. The third container 390C is connected to the second container 390B and the suction hole of the pump 310. Water W2 is stored in the third container 390C. A pipe 336 is inserted into the third container 390C, and an end portion of the pipe 336 is immersed in the water W2. The third container 390C adjusts the drawing pressure at which the pump 310 draws in the air in accordance with the water level of the water W2 and the air that flows into the pipe 336 from the end portion of the pipe 336.

The valve 101 is mounted on a top surface of the third container 390C so as to block the connection hole 392, which is an exit of the third container 390C.

In the above-described configuration, the suction port 391 is connected to the container 390A via the tube 330. The first ventilation hole 111 of the valve 101 is connected to the connection hole 392 of the suction unit 309. The second ventilation hole 112 of the valve 101 is connected to the suction hole of the pump 310 via a tube 337. The third ventilation hole 113 of the valve 101 is opened under atmospheric pressure.

The flow of the air in the fluid control device 300 during the period when the pump 310 is driven is the same as the flow of the air in the fluid control device 100 illustrated in FIG. 8.

The flow of the air in the fluid control device 300 when driving of the pump 310 is discontinued, when the pressure in the container 390A reaches a maximum drawing pressure of the pump 310, or when a flow path is blocked is also the same as the flow of the air in the fluid control device 100 illustrated in FIG. 9.

For example, the suction port 391 is blocked if human body tissue is sucked in through the suction port 391 in a state where there is no target to be sucked in. As a result of the suction port 391 being blocked, the pressure in the first region becomes equal to or lower than the pressure in the second region. When the pressure in the first region has become equal to or lower than the pressure in the second region, the diaphragm 120 automatically opens the third ventilation hole 113 and the hole 122, and the suction port 391 is released under atmospheric pressure.

Accordingly, the valve 101 can cause the pressure in the third container 390C to become a negative pressure by drawing in the air from the third container 390C and then can rapidly restore the pressure in the third container 390C to atmospheric pressure by causing the air to flow into the third container 390C.

In case of pneumothorax, when a wound has become small and the flow rate has started decreasing, it is said that a healing period can be further shortened by stopping a suction operation. Thus, the valve 101, which automatically opens the suction port 391, may preferably be used in treatment for pneumothorax.

In addition, since the structure of the valve 101 is simple and inexpensive, the suction unit 309 and the valve 101 can be used as disposable members. Therefore, the valve 101 can reduce the costs for maintenance of a hospital.

Advantageous effects similar to the above can be obtained by the fluid control device 300 that includes the valve 101.

A fluid control device 400 according to a fourth embodiment of the present disclosure will be described below.

Figure 13:
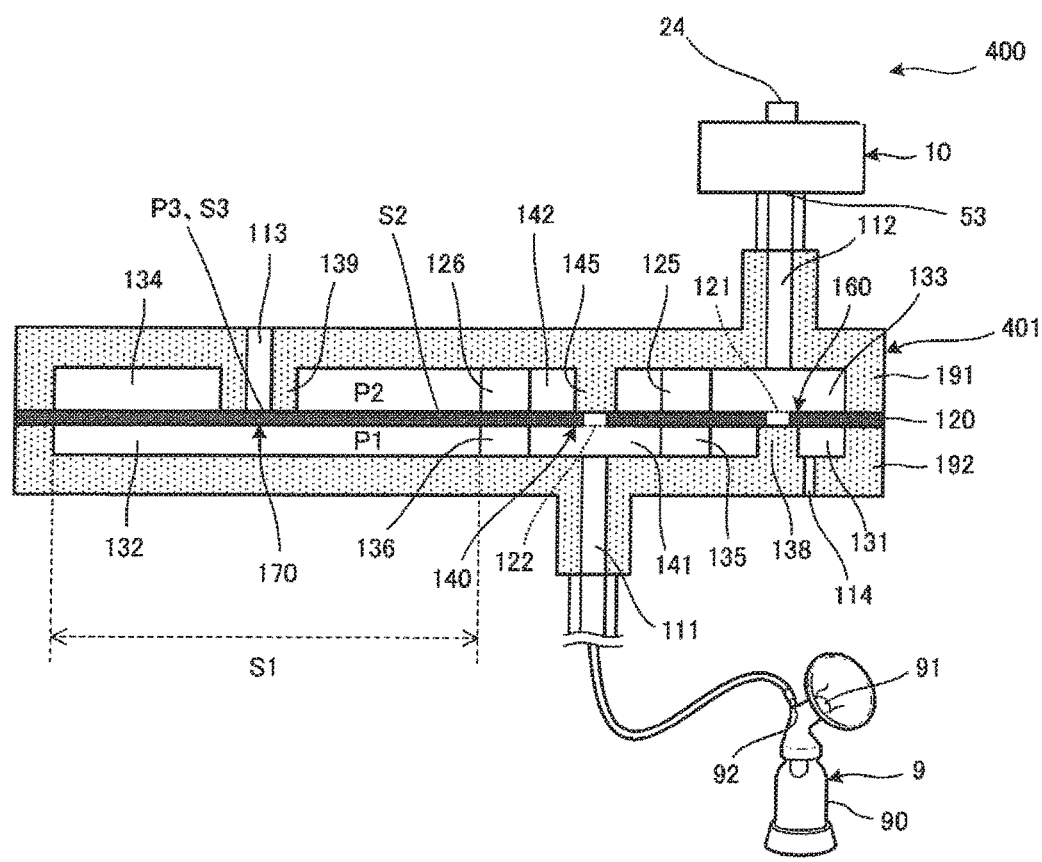
FIG. 13 is a diagram illustrating the appearance of a fluid control device 400 according to a fourth embodiment of the present disclosure.

FIG. 13 is a sectional view of the fluid control device 400 according to the fourth embodiment of the present disclosure. The difference between the fluid control device 400 and the fluid control device 100 is a valve 401. The difference between the valve 401 and the valve 101 is that the valve 401 has a fourth ventilation hole 114. The diameter of the fourth ventilation hole 114 is smaller than the diameter of the first ventilation hole 111. In addition, the diameter of the fourth ventilation hole 114 is smaller than the diameter of the second ventilation hole 112. Note that the rest of the configuration of the fluid control device 400 is the same as that of the fluid control device 100, and thus, the description thereof will be omitted.

The flow of air in the fluid control device 400 will now be described. The flow of the air in the fluid control device 400 is classified into a first stage, a second stage, and a third stage. The first stage corresponds to the period from when driving of the piezoelectric pump 10 is started until the pressure in the container 90 reaches a maximum drawing pressure of the piezoelectric pump 10. The second stage corresponds to the period from when the pressure in the container 90 reaches the maximum drawing pressure of the piezoelectric pump 10 until driving of the piezoelectric pump 10 is discontinued. The third stage corresponds to the time immediately after driving of the piezoelectric pump 10 has been discontinued.

Figure 14:
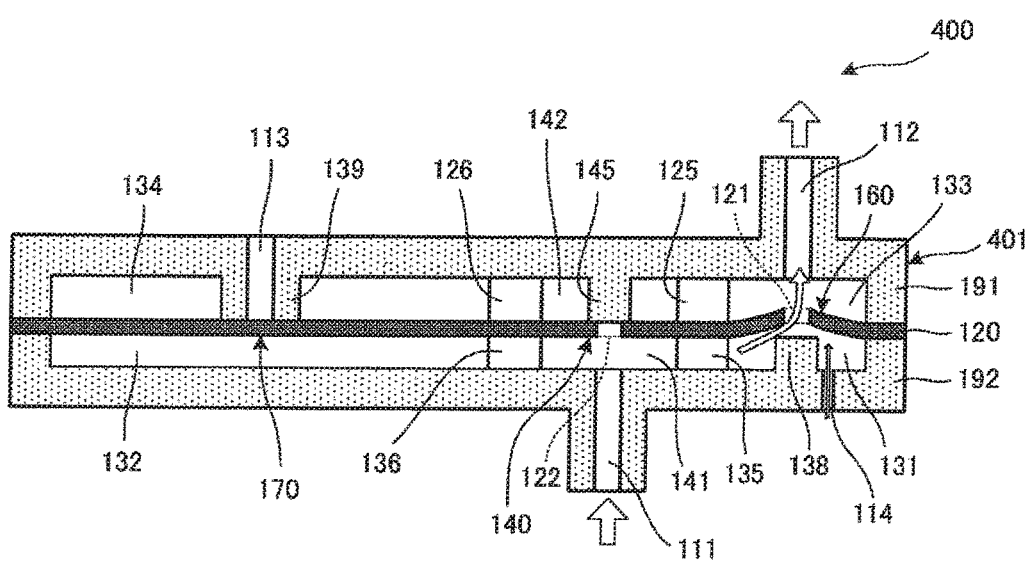
FIG. 14 is a diagram illustrating the flow of the air in the fluid control device 400 during the period from when driving of the piezoelectric pump 10 is started until the pressure in the container 90 reaches the maximum drawing pressure.

The flow of the air in the first stage will be described first. FIG. 14 is a diagram illustrating the flow of the air in the fluid control device 400 during the period from when driving of the piezoelectric pump 10 is started until the pressure in the container 90 reaches the maximum drawing pressure. Arrows in FIG. 14 indicate the flow of the air. In FIG. 14, the piezoelectric pump 10 and the suction unit 9 are not illustrated.

First, a user places the suction port 91 of the suction unit 9 onto, for example, a human breast or an animal breast. The pressure in the container 90 before the piezoelectric pump 10 is driven is at atmospheric pressure. The fluid control device 400 switches the piezoelectric pump 10 on when suction of a liquid using the suction unit 9 is started.

Once the piezoelectric pump 10 has been driven, the air in the second upper valve chamber 133 is drawn into the piezoelectric pump 10 via the second ventilation hole 112 and the suction hole 53. Then, the air in the piezoelectric pump 10 is discharged through the discharge hole 24.

As a result, in the check valve 140, the pressure in the first lower valve chamber 141 is higher than the pressure in the first upper valve chamber 142. Thus, the portion of the diaphragm 120 around the periphery of the hole 122 is maintained in contact with the valve seat 145 and interrupts the communication between the first lower valve chamber 141 and the first upper valve chamber 142.

In the check valve 160, the pressure in the second lower valve chamber 131 is higher than the pressure in the second upper valve chamber 133. Thus, in the check valve 160, the portion of the diaphragm 120 around the periphery of the hole 121 moves out of contact with the valve seat 138, and the first ventilation hole 111 and the second ventilation hole 112 are caused to communicate with each other via the hole 121.

In the exhaust valve 170, the pressure in the third lower valve chamber 132 is higher than the pressure in the third upper valve chamber 134. Thus, the diaphragm 120 seals the third ventilation hole 113 and interrupts the communication between the second ventilation hole 112 and the third ventilation hole 113.

In other words, in the valve 401, in the case where the pressure in the first region is higher than the pressure in the second region, the first ventilation hole 111 and the second ventilation hole 112 are caused to communicate with each other, and the communication between the first ventilation hole 111 and the third ventilation hole 113 and the communication between the second ventilation hole 112 and the third ventilation hole 113 are interrupted.

As a result, the air in the container 90 of the suction unit 9 is discharged from the connection hole 92 toward the first lower valve chamber 141 of the valve 401 via the first ventilation hole 111. Consequently, the pressure (air pressure) in the container 90 is reduced to be lower than atmospheric pressure and becomes a negative pressure.

Therefore, the suction unit 9 can suck a liquid (e.g., breast milk or the like) outside the container 90 into the container 90 through the suction port 91. The suction unit 9 stores the liquid in the container 90 and discharges the air in the container 90 through the connection hole 92.

Note that the air discharged to the first lower valve chamber 141 flows into the second upper valve chamber 133 via the communication path 135, the second lower valve chamber 131, and the hole 121. Then, the air in the second upper valve chamber 133 is drawn into the piezoelectric pump 10 via the second ventilation hole 112 and the suction hole 53 and is discharged through the discharge hole 24.

Here, in the fluid control device 400, a small portion of the air outside the valve 401 is drawn into the valve 401 via the fourth ventilation hole 114. Thus, in the fluid control device 400, the flow rate of the air that is drawn in from the container 90 is smaller than that in the fluid control device 100.

However, since the diameter of the fourth ventilation hole 114 is very small compared with the diameter of the first ventilation hole 111, the influence of the fourth ventilation hole 114 is small. Consequently, the air is drawn into the valve 401 mainly through the first ventilation hole 111, and the air flows from the container 90 toward the piezoelectric pump 10. As a result, in the exhaust valve 170, a relationship of P2<P1 and the relationship of S1×(P1−P2)>S3×(P3−P1) are satisfied.

Figure 15:
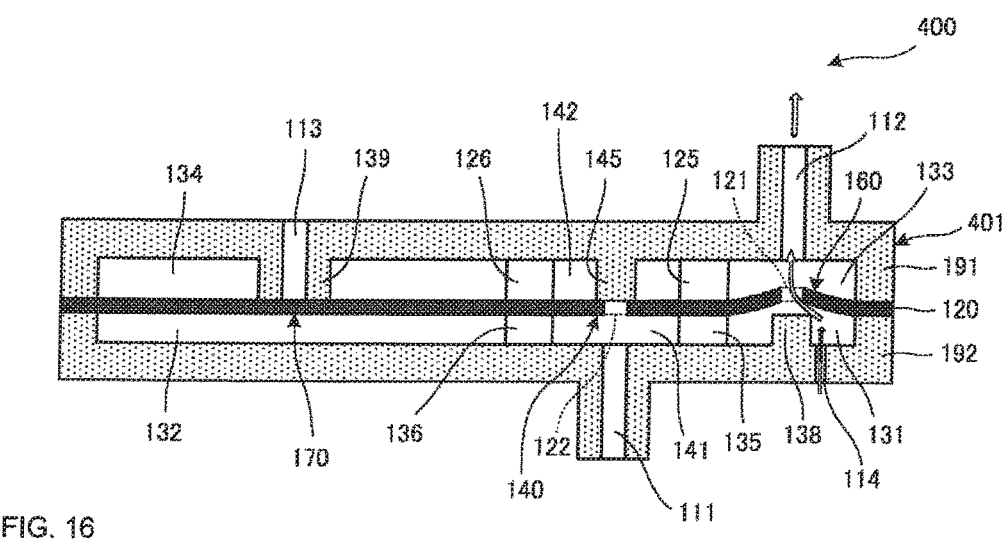
FIG. 15 is a diagram illustrating the flow of the air in the fluid control device 400 during the period from when the pressure in the container 90 reaches the maximum drawing pressure until driving of the piezoelectric pump 10 is discontinued.

The flow of the air in the second stage will now be described. FIG. 15 is a diagram illustrating the flow of the air in the fluid control device 400 during the period from when the pressure in the container 90 reaches the maximum drawing pressure until driving of the piezoelectric pump 10 is discontinued. Arrows in FIG. 15 indicate the flow of the air. In FIG. 15, the piezoelectric pump 10 and the suction unit 9 are not illustrated.

When the container 90 is sufficiently decompressed, the piezoelectric pump 10 cannot draw in the air from the container 90. However, in the second stage, the air is drawn in through the fourth ventilation hole 114 and flows into the piezoelectric pump 10 by passing the hole 121 of the check valve 160. Consequently, in the exhaust valve 170, a relationship of P2<P1 and the relationship of S1×(P1−P2)>S3×(P3−P1) are satisfied.

As a result, the fluid control device 400 maintains a state where the third ventilation hole 113 is closed. In other words, the fluid control device 400 can maintain a decompressed state of the container 90 during the period when the piezoelectric pump 10 is kept driven.

Figure 16:
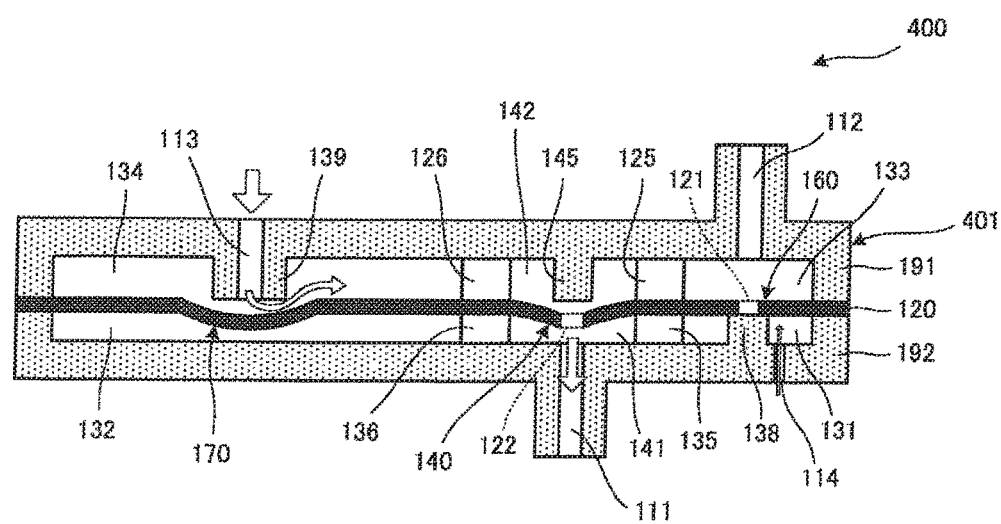
FIG. 16 is a diagram illustrating the flow of the air in the fluid control device 400 immediately after driving of the piezoelectric pump 10 has been discontinued.

The flow of the air in the third stage will now be described. FIG. 16 is a diagram illustrating the flow of the air in the fluid control device 400 immediately after driving of the piezoelectric pump 10 has been discontinued. Arrows in FIG. 16 indicate the flow of the air. In FIG. 16, the piezoelectric pump 10 and the suction unit 9 are not illustrated.

When suction of a liquid using the suction unit 9 is terminated, the fluid control device 400 switches the piezoelectric pump 10 off and discontinues driving of the piezoelectric pump 10. In this case, the pressure in the valve 401 is lower than atmospheric pressure. Thus, a small portion of the air outside the valve 401 is drawn into the valve 401 through the fourth ventilation hole 114.

However, since the diameter of the fourth ventilation hole 114 is very small compared with the diameter of the second ventilation hole 112, the influence of the fourth ventilation hole 114 is small. Consequently, a small portion of the air flows into the piezoelectric pump 10 mainly through the discharge hole 24 of the piezoelectric pump 10 and flows into the second region via the suction hole 53 and the second ventilation hole 112.

As a result, in the check valve 160, the pressure in the second lower valve chamber 131 is reduced to be lower than the pressure in the second upper valve chamber 133. Thus, the diaphragm 120 closes the hole 121 by coming into contact with the valve seat 138.

In the check valve 140, the pressure in the first lower valve chamber 141 is reduced to be lower than the pressure in the first upper valve chamber 142. Consequently, the portion of the diaphragm 120 around the periphery of the hole 122 moves out of contact with the valve seat 145 and causes the first ventilation hole 111 and the second region to communicate with each other.

In the exhaust valve 170, the pressure of the third lower valve chamber 132 is reduced to be lower than the pressure in the third upper valve chamber 134. In other words, in the exhaust valve 170, a relationship of pressure P2 P1 and a relationship of S1×(P1−P2)<S3×(P3−P1) are satisfied.

Accordingly, the diaphragm 120 opens the third ventilation hole 113 by moving out of contact with the valve seat 139.

In other words, in the valve 401, in the case where the pressure in the first region is lower than the pressure in the second region, the first ventilation hole 111 and the third ventilation hole 113 are caused to communicate with each other. As a result, the air rapidly flows through the third ventilation hole 113 into the container 90 via the third upper valve chamber 134, the communication path 126, the first upper valve chamber 142, the hole 122, the first lower valve chamber 141, and the first ventilation hole 111 (see FIG. 9).

This causes an increase in the pressure (air pressure) in the container 90 and restores the pressure in the container 90 to atmospheric pressure. Accordingly, the suction port 91 of the suction unit 9 can be easily removed from a human breast or an animal breast.

Therefore, the valve 401 can cause the pressure in the container 90 to become a negative pressure by drawing in the air from the container 90 and then can rapidly restore the pressure in the container 90 to atmospheric pressure by causing the air to flow into the container 90. In addition, advantageous effects similar to the above can be obtained by the fluid control device 400 that includes the valve 401 according to the present embodiment.

Other Embodiments

Note that, although the air is used as a gas in the above-described embodiments, the gas is not limited to the air, and the present disclosure can be applied to a case where the gas is a gas other than the air.

In the above-described embodiments, although a case has been described in which a liquid is sucked in by the suction unit, a target to be sucked in may be a material (e.g., a gel-like material) other than a liquid.

Although the piezoelectric pump 10 according to the above-described embodiments includes a unimorph-type actuator that performs bending vibration, the piezoelectric pump 10 may include a bimorph-type actuator in which a piezoelectric element is attached to each of the two surfaces of a vibrating plate and which performs bending vibration.

Although the piezoelectric pump 10 according to the above-described embodiments includes an actuator that performs bending vibration by expansion and contraction of the piezoelectric element 40, the piezoelectric pump 10 is not limited to having this configuration. For example, the piezoelectric pump 10 may include an actuator that performs bending vibration as a result of being electromagnetically driven.

Although the piezoelectric element 40 is formed from a PZT-based ceramic in the above-described embodiments, the material of the piezoelectric element 40 is not limited to this. For example, the piezoelectric element 40 may be formed from a piezoelectric material of a non-lead-based piezoelectric ceramic, such as a potassium-sodium niobate-based ceramic or an alkali niobate-based ceramic, or the like.

Lastly, the descriptions of the above-described embodiments are examples in all respects, and the present disclosure is not to be considered limited to the embodiments. The scope of the present disclosure is to be determined not by the above-described embodiments, but by the claims. In addition, it is intended that meanings equal to the claims and all the modifications within the scope of the claims are included in the scope of the present disclosure.

9 suction unit
10 piezoelectric pump
17 outer housing
18 nozzle
24 discharge hole
31 ventilation path
36 pump chamber
37 top plate
38 side plate
39 vibrating plate
40 piezoelectric element
42 cap
45 ventilation hole
52 projecting portion
53 suction hole
55A to 55D cutout portion
56A to 56D threaded hole
61 center portion
62 projecting portion
63, 72 external terminal
70 electrode-conduction plate
73 inner terminal
90 container
91 suction port
92 connection hole
100, 200, 300, 400 fluid control device
101. 201, 401 valve
111 first ventilation hole
112 second ventilation hole
113 third ventilation hole
114 fourth ventilation hole
120 diaphragm
121, 122 hole
125, 126 communication path
131 second lower valve chamber
132 third lower valve chamber
133 second upper valve chamber
134 third upper valve chamber
135, 136 communication path
138, 139 valve seat
140 check valve
141 first lower valve chamber
142 first upper valve chamber
145 valve seat
151 first seal member
152 second seal member
160 check valve
170 exhaust valve
191 first valve housing
192 second valve housing
209 suction unit
210 pump
215 pressure gauge
250 filter
253 suction hole
290 container
291 suction port
292 connection hole
293 second housing
294, 295, 296 tube
308 patient
309 suction unit
310 pump
330 tube
336 pipe
390A first container
390B second container
390C third container 391 suction port
392 connection hole

The invention claimed is:

1. A valve comprising:
a valve housing comprising a first ventilation hole, a second ventilation hole, and a third ventilation hole; and
a diaphragm dividing the valve housing into a first region and a second region, wherein the first region is in communication with the first ventilation hole, and the second region is in communication with the second ventilation hole,
wherein the diaphragm is fixed to the valve housing such that:
when a pressure in the first region is higher than a pressure in the second region, the diaphragm causes the first ventilation hole and the second ventilation hole to communicate with each other and interrupts a communication between the first ventilation hole and the third ventilation hole and a communication between the second ventilation hole and the third ventilation hole, and
when the pressure in the first region is lower than the pressure in the second region, the diaphragm causes the first ventilation hole and the third ventilation hole to communicate with each other through a first aperture in the diaphragm.

2. The valve according to claim 1,
wherein the diaphragm moves into and out of contact with a portion of the valve housing due to a pressure difference between the first region and the second region and performs switching of a communication state between the first ventilation hole and the third ventilation hole.

3. The valve according to claim 2,
wherein the portion of the valve housing comprises a first valve seat in the second region that projects toward the diaphragm,
and
wherein the diaphragm is fixed to the valve housing such that a portion of the diaphragm around a periphery of the first aperture is in contact with the first valve seat.

4. The valve according to claim 3,
wherein the portion of the valve housing comprises a second valve seat in the second region that projects toward the diaphragm,
wherein the second valve seat defines the third ventilation hole, and
wherein the diaphragm is fixed to the valve housing such that the diaphragm is in contact with the second valve seat.

5. The valve according to claim 3,
wherein the valve housing comprises a second valve seat in the first region that projects toward the diaphragm,
wherein the diaphragm comprises a second aperture, and
wherein the diaphragm is fixed to the valve housing such that a portion of the diaphragm around a periphery of the second aperture is in contact with the second valve seat.

6. The valve according to claim 3, wherein the valve housing comprises a fourth ventilation hole being in communication with the first region.

7. A fluid control device comprising:
a pump having a suction hole for a gas and a discharge hole for the gas;
a suction unit having a suction port for sucking a fluid and a connecting portion; and
the valve according to claim 3,
wherein the first ventilation hole is connected to the connecting portion of the suction unit, and
wherein the second ventilation hole is connected to the suction hole of the pump.

8. The valve according to claim 2,
wherein the portion of the valve housing comprises a valve seat in the second region that projects toward the diaphragm,
wherein the valve seat defines the third ventilation hole, and
wherein the diaphragm is fixed to the valve housing such that the diaphragm is in contact with the valve seat.

9. The valve according to claim 8,
wherein the valve housing comprises a second valve seat in the first region that projects toward the diaphragm,
wherein the diaphragm comprises a second aperture, and
wherein the diaphragm is fixed to the valve housing such that a portion of the diaphragm around a periphery of the second aperture is in contact with the second valve seat.

10. The valve according to claim 8, wherein the valve housing comprises a fourth ventilation hole being in communication with the first region.

11. A fluid control device comprising:
a pump having a suction hole for a gas and a discharge hole for the gas;
a suction unit having a suction port for sucking a fluid and a connecting portion; and
the valve according to claim 8,
wherein the first ventilation hole is connected to the connecting portion of the suction unit, and
wherein the second ventilation hole is connected to the suction hole of the pump.

12. The valve according to claim 2,
wherein the valve housing comprises a valve seat in the first region that projects toward the diaphragm,
wherein the diaphragm comprises a second aperture, and
wherein the diaphragm is fixed to the valve housing such that a portion of the
diaphragm around a periphery of the second aperture is in contact with the valve seat.

13. The valve according to claim 2, wherein the valve housing comprises a fourth ventilation hole being in communication with the first region.

14. A fluid control device comprising:
a pump having a suction hole for a gas and a discharge hole for the gas;
a suction unit having a suction port for sucking a fluid and a connecting portion; and
the valve according to claim 2,
wherein the first ventilation hole is connected to the connecting portion of the suction unit, and
wherein the second ventilation hole is connected to the suction hole of the pump.

15. The valve according to claim 1,
wherein the valve housing comprises a valve seat in the first region that projects toward the diaphragm,
wherein the diaphragm comprises a second aperture, and
wherein the diaphragm is fixed to the valve housing such that a portion of the diaphragm around a periphery of the second aperture is in contact with the valve seat.

16. The valve according to claim 15, wherein the valve housing comprises a fourth ventilation hole being in communication with the first region.

17. A fluid control device comprising:
a pump having a suction hole for a gas and a discharge hole for the gas;
a suction unit having a suction port for sucking a fluid and a connecting portion; and
the valve according to claim 15,
wherein the first ventilation hole is connected to the connecting portion of the suction unit, and
wherein the second ventilation hole is connected to the suction hole of the pump.

18. The valve according to claim 1, wherein the valve housing comprises a fourth ventilation hole being in communication with the first region.

19. A fluid control device comprising:
a pump having a suction hole for a gas and a discharge hole for the gas;
a suction unit having a suction port for sucking a fluid and a connecting portion; and
the valve according to claim 1,
wherein the first ventilation hole is connected to the connecting portion of the suction unit, and
wherein the second ventilation hole is connected to the suction hole of the pump.

20. The fluid control device according to claim 19, wherein the suction unit includes
a first container connected to the suction port, wherein the first container stores a fluid sucked in through the suction port,
a second container connected to the first container, wherein the second container allows the gas to pass through the second container and hinders the fluid from passing through the second container, and
a third container connected to the second container and the suction hole of the pump, wherein the third container adjusts a drawing pressure of the gas drawn by the pump.

21. The valve according to claim 1, wherein:
the valve housing comprises a first valve seat in the second region that projects toward the diaphragm,
the housing comprises a second valve seat in the second region that projects toward the diaphragm, the second valve seat defining the third ventilation hole,
the valve housing comprises a third valve seat in the first region that projects toward the diaphragm,
the diaphragm further comprises a second aperture,
the diaphragm is fixed to the valve housing such that a portion of the diaphragm around a periphery of the first aperture is in contact with the first valve seat, and
the diaphragm is fixed to the valve housing such that a portion of the diaphragm around a periphery of the second aperture is in contact with the third valve seat.

22. The valve according to claim 1, wherein:
the valve housing comprises a first valve seat, a second valve seat, and a third valve seat,
the diaphragm further comprises a second aperture,
the third valve seat is arranged in the first region and projects toward the diaphragm, and
the diaphragm is fixed to the valve housing such that a portion of the diaphragm around a periphery of the second aperture is in contact with the third valve seat.

* * * * *